(12) United States Patent
Sekimoto

(10) Patent No.: US 9,297,777 B2
(45) Date of Patent: Mar. 29, 2016

(54) ANALYZING DEVICE, SENSOR TESTING DEVICE, TESTING METHOD AND COMPUTER-READABLE STORAGE MEDIUM

(75) Inventor: Shinjiro Sekimoto, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 257 days.

(21) Appl. No.: 13/365,054

(22) Filed: Feb. 2, 2012

(65) Prior Publication Data

US 2012/0199496 A1    Aug. 9, 2012

(30) Foreign Application Priority Data

Feb. 3, 2011  (JP) .................................. 2011-021942
Feb. 3, 2011  (JP) .................................. 2011-021943
Dec. 27, 2011 (JP) .................................. 2011-286060

(51) Int. Cl.
*G01N 27/416* (2006.01)
*G01N 27/327* (2006.01)
*A61B 5/145* (2006.01)
*A61B 5/1486* (2006.01)

(52) U.S. Cl.
CPC .......... *G01N 27/3274* (2013.01); *A61B 5/1486* (2013.01); *A61B 5/14532* (2013.01)

(58) Field of Classification Search
USPC ............. 205/791.5; 204/401, 403.01–403.15, 204/406; 600/345, 347
See application file for complete search history.

(56) References Cited

U.S. PATENT DOCUMENTS

| | | | |
|---|---|---|---|
| 5,266,179 A | 11/1993 | Nankai et al. | 204/40 |
| 5,411,647 A | 5/1995 | Johnson et al. | 204/153.1 |
| 5,846,744 A | 12/1998 | Athey et al. | 435/7.9 |
| 6,121,009 A | 9/2000 | Heller et al. | 435/14 |
| 6,895,263 B2 | 5/2005 | Shin et al. | 600/316 |
| 7,122,110 B2 | 10/2006 | Deng et al. | 205/777.5 |
| 7,132,041 B2 | 11/2006 | Deng et al. | 205/777.5 |
| 7,190,988 B2 | 3/2007 | Say et al. | 600/345 |
| 2005/0103625 A1* | 5/2005 | Rhodes et al. | 204/403.11 |
| 2009/0184004 A1 | 7/2009 | Chatelier et al. | |

FOREIGN PATENT DOCUMENTS

| | | | | |
|---|---|---|---|---|
| EP | 1455182 A1 | | 9/2004 | |
| GB | 2296332 A | | 6/1996 | |
| JP | 2004-233294 | * | 5/2004 | ............. G01N 27/26 |
| JP | 2004-233294 | * | 8/2004 | ............. G01N 27/26 |
| WO | WO 2010/106781 | | 9/2010 | ............. A61B 5/1473 |

OTHER PUBLICATIONS

Extended European Search Report issued in corresponding European Patent Application No. 12153538.9 dated Apr. 4, 2012.

*Primary Examiner* — Luan Van
*Assistant Examiner* — Steven Rosenwald
(74) *Attorney, Agent, or Firm* — Morgan, Lewis & Bockius LLP

(57) ABSTRACT

There is provided a sensor testing method including: applying at least one of a first voltage that obtains a response caused by a substance and a second voltage that either obtains no response or substantially no response caused by the substance across a first electrode and a second electrode of a sensor; measuring current flowing between the first electrode and the second electrode; and determining whether or not there is a defect present in the sensor based on a quantity related to an amount of change per specific period of time of a current measured when the first voltage and/or the second voltage have been applied.

10 Claims, 19 Drawing Sheets

(1)  (2)

(3)  (4)  (5)  (6)

ANALYZING DEVICE, SENSOR TESTING DEVICE, TESTING METHOD AND COMPUTER-READABLE STORAGE MEDIUM

CROSS-REFERENCE TO RELATED APPLICATIONS

This application claims priority to JP Application No. 2011-021942, filed Feb. 3, 2011, JP Application No. 2011-021943, filed Feb. 3, 2011, and JP Application No. 2011-286060, filed Dec. 27, 2011, all of which are hereby incorporated by reference in their entirety.

BACKGROUND

1. Technical Field

The present invention relates to an analyzing device, a sensor testing device, testing method and computer-readable storage medium.

2. Related Art

There is a related proposal for an electro-chemical biosensor in which plural sets of a working electrode and a counter electrode are provided, and a defect of a sensor is detected by comparing responses between each electrode set (see for example specifications of U.S. Pat. No. 7,190,988 and U.S. Pat. No. 6,121,009).

There is also a proposal for a method to adjust data collected from a sensor in an electro-chemical biosensor (see for example the specification of U.S. Pat. No. 6,895,263). In the technology of the specification of U.S. Pat. No. 6,895,263 the correction characteristics are computed based on a current sensor data point, and a possible error or a sensitivity change is ascertained from the correction characteristics. In order to determine whether or not the correction characteristics at this time are unpredictable a comparison is made between an estimated value related to the correction characteristics and the correction characteristics at this time, so as to ascertain a fault in the sensor or a change in sensor sensitivity. The estimated value related to the correction characteristics is determined from the correction characteristics at that time and from past correction characteristics, and a faulty sensor is determined when at least two unpredictable correction characteristics are received in a row that do not support each other.

There is also a proposal for an electro-chemical sensor monitoring device installed with an electro-chemical sensor formed from two electrode sets or three electrode sets, in which the current flowing between a working electrode and a counter electrode is detected, a transient response time until current reaches a steady state is counted, and the sensor quality is determined with reference to the relationship between the transient response time and correction values (see for example Japanese Patent Application Laid-Open (JP-A) No. 2004-233294).

However, since a relative comparison is performed between plural sets of working electrode and counter electrode provided in the technology of U.S. Pat. Nos. 7,190,988 and 6,121,009, this technology is not able to ascertain whether or not each of the electrode sets is normal in absolute terms. In particular, since electrode sets in electro-chemical biosensors are miniature in size it is conceivable that all of the electrode sets within a sensor are damaged at the same time, and an issue arises that it is not possible to stably test the sensor state by performing relative comparison. Furthermore, since plural sets of electrodes are required this is also detrimental from the perspectives of manufacturing and cost.

In the technology of U.S. Pat. No. 6,895,263 there is uncertainty to determination since a faulty sensor is determined based on an estimated value computed employing sampled data.

In the technology of JP-A No. 2004-233294 there is an issue in that the time until a steady state is reached may become long.

SUMMARY

In consideration of the above circumstances the present invention is directed towards an analyzing device capable of stably testing the state of a sensor in a short time, without providing plural electrode sets, and to a sensor testing device, testing method and computer-readable storage medium of the same.

An analyzing device according to the first aspect of the present invention includes: a sensor section including a reagent layer including a reagent that reacts with a substance in a sample liquid, an electrode including a first electrode and a second electrode for applying a voltage to the reagent layer, and an external layer membrane for making contact with the reagent layer; a voltage application unit for applying across the first electrode and the second electrode at least one of a first voltage that obtains a response caused by the substance and a second voltage that either obtains no response or substantially no response caused by the substance; a current measurement unit for measuring current flowing between the first electrode and the second electrode; and a determination unit for determining whether or not there is a defect present in the external layer membrane based on at least one of a first physical quantity related to an amount of change per specific period of time of a first current measured by the current measurement unit when the first voltage has been applied and a second physical quantity related to an amount of change per specific period of time of a second current measured by the current measurement unit when the second voltage has been applied.

According to the above analyzing device, a sensor section has a reagent layer including a reagent that reacts with a substance in a sample liquid, an electrode including a first electrode and a second electrode for applying a voltage to the reagent layer, and an external layer membrane for making contact with the reagent layer. When the voltage application unit applies across the first electrode and the second electrode at least one of a first voltage that obtains a response caused by the substance and a second voltage that either obtains no response or substantially no response caused by the substance, a current measurement unit measures current flowing between the first electrode and the second electrode. Then, the determination unit determines whether or not there is a defect present in the external layer membrane based on at least one of a first physical quantity related to an amount of change per specific period of time of a first current measured by the current measurement unit when the first voltage has been applied and a second physical quantity related to an amount of change per specific period of time of a second current measured by the current measurement unit when the second voltage has been applied. The first physical quantity and the second physical quantity may be amount of change per specific period of time of the respective currents themselves, or other physical quantities that can be derived therefrom.

Accordingly, by employing the physical quantity related to amount of change in the current when at least one of the first voltage that obtains a response caused by the substance and the second voltage that either obtains no response or substantially no response caused by the substance to test the state of the external layer membrane, the state of the sensor can be tested stably and in a short time without providing plural sets of electrodes.

The first physical quantity may be a first time from until the amount of change per specific period of time of the first current reaches a value in a predetermined first specific range and the second physical quantity may be a second time until the amount of change per specific period of time of the second current reaches a value in a predetermined second specific range. By using such quantities, a defect present in the external layer membrane can be detected in shorter time as compared to cases employing the time for current to reach a steady state.

The analyzing device may further include a correction unit that corrects the current value measured by the current measurement unit when a defect is determined by the determination unit to have occurred in the external layer membrane, the correction unit performing correction based on at least one of a predetermined first relationship between the first physical quantity and a defect ratio of the external layer membrane and a predetermined second relationship between the second physical quantity and a defect ratio of the external layer membrane. In other words, the first physical quantity and the second physical quantity obtained when the first voltage and the second voltage are respectively applied change in response to the defect ratio of the external layer membrane. Therefore, the measured current value can be corrected based on the defect ratio derived from these physical quantities. More specifically, the correction unit may estimate the defect ratio based on at least one of the first relationship and the second relationship, and correct the current value measured by the current measurement unit based on a predetermined relationship between the defect ratio of the external layer membrane and the current value measured from the sensor section provided with an external layer membrane having defects corresponding to the defect ratio.

When the correction unit estimates the defect ratio based on both the first relationship and the second relationship, the correction unit may compute the defect ratio as the average value, the maximum value or the minimum value of a first defect ratio estimated based on the first relationship and a second defect ratio estimated based on the second relationship.

The analyzing device may further include an output unit that outputs a signal indicating that a defect has occurred in the sensor section when a defect is determined to have occurred in the external layer membrane by the determination unit.

In the analyzing device, when applying both the first voltage and the second voltage the voltage application unit may apply the first voltage and the second voltage alternately.

In the analyzing device, the current measurement unit may continuously measure the current flowing between the first electrode and the second electrode, and the determination unit may determine the presence or absence of a defect in the external layer membrane at a predetermined timing. Since it is desirable to be able to test the sensor in a short time in a device that continuously monitors current in this manner such as, for example, in a continuous blood sugar monitoring device, application of the analyzing device of the present invention is highly effective.

During use of the analyzing device the sensor section may be disposed under the skin of a user of the analyzing device and the reagent layer reacts to a composition to be tested present under the skin.

Moreover, the reagent layer may extract electrons from the composition to be tested and may supply the extracted electrons to the electrode.

Furthermore, the reagent layer may include an enzyme portion for extracting electrons from the composition to be tested.

A sensor testing device according to the second aspect of the present invention includes: a voltage application unit that applies at least one of a first voltage that obtains a response caused by a substance and a second voltage that either obtains no response or substantially no response caused by the substance across a first electrode and a second electrode of a sensor section configured with a reagent layer including a reagent that reacts with the substance in a sample liquid, an electrode including the first electrode and the second electrode for applying a voltage to the reagent layer, and an external layer membrane for making contact with the reagent layer; a current measurement unit that measures current flowing between the first electrode and the second electrode; and a determination unit that determines whether or not there is a defect present in the external layer membrane based on at least one of a first physical quantity related to an amount of change per specific period of time of a first current measured by the current measurement unit when the first voltage has been applied and a second physical quantity related to an amount of change per specific period of time of a second current measured by the current measurement unit when the second voltage has been applied. For instance, the present device can be employed to test the state of the external layer membrane of sensors in a sensor manufacturing process, such as in a factory where sensors are being manufactured.

A sensor testing method according to the third aspect of the present invention includes: applying at least one of a first voltage that obtains a response caused by a substance and a second voltage that either obtains no response or substantially no response caused by the substance across a first electrode and a second electrode of a sensor section configured with a reagent layer including a reagent that reacts with the substance in a sample liquid, an electrode including the first electrode and the second electrode for applying a voltage to the reagent layer, and an external layer membrane for making contact with the reagent layer; measuring current flowing between the first electrode and the second electrode; and determining whether or not there is a defect present in the external layer membrane based on at least one of a first physical quantity related to an amount of change per specific period of time of a first current measured when the first voltage has been applied and a second physical quantity related to an amount of change per specific period of time of a second current measured when the second voltage has been applied.

The fourth aspect of the present invention is a computer-readable storage medium storing a program for causing a computer to execute a sensor testing method, the sensor testing method including: by a voltage application unit, applying at least one of a first voltage that obtains a response caused by a substance and a second voltage that either obtains no response or substantially no response caused by the substance across a first electrode and a second electrode of a sensor section configured with a reagent layer including a reagent that reacts with the substance in a sample liquid, an electrode including the first electrode and the second electrode for applying a voltage to the reagent layer, and an external layer membrane for making contact with the reagent layer; by a current measurement unit, measuring current flowing between the first electrode and the second electrode; and by a determination unit, determining whether or not there is a defect present in the external layer membrane based on at least one of a first physical quantity related to an amount of change per specific period of time of a first current measured by the current measurement unit when the first voltage has been applied and a second physical quantity related to an amount of change per specific period of time of a second current measured by the current measurement unit when the second voltage has been applied.

Accordingly, by employing the physical quantity related to amount of change in the current when at least one of the first voltage that obtains a response caused by the substance and the second voltage that either obtains no response or substantially no response caused by the substance to test the state of the external layer membrane, the state of the sensor can be tested stably and in a short time without providing plural sets of electrodes.

BRIEF DESCRIPTION OF THE DRAWINGS

Exemplary embodiments of the present invention will be described in detail based on the following figures, wherein.

DETAILED DESCRIPTION

Explanation follows regarding an exemplary embodiment of the present invention, with respect to the drawings. In the present exemplary embodiment explanation is given of a case in which the analyzing device of the present invention is applied to a Continuous Glucose Monitoring (CGM) device.

First Exemplary Embodiment

Figure 1:
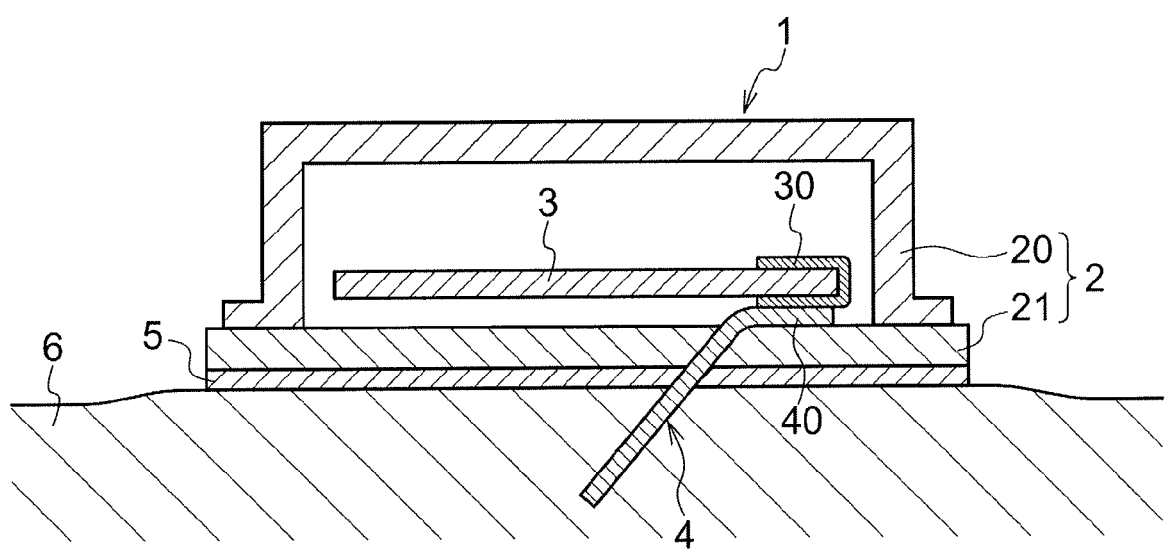
FIG. 1 is a cross-section illustrating a continuous glucose monitoring device of an exemplary embodiment.

As shown in FIG. 1, a continuous glucose monitoring device 1 of the present exemplary embodiment is configured including a housing 2, a circuit board 3, and a sensor section 4. The continuous glucose monitoring device 1 is applied to skin 6 such as an abdominal or shoulder region of a human body, and continuously monitors the concentration of glucose in the blood or in interstitial subcutaneous fluid.

The housing 2 is configured with a cover 20 and a base 21 forming the external profile of the continuous glucose monitoring device 1. The cover 20 and the base 21 are joined together so as to house the circuit board 3 in the space formed between the cover 20 and the base 21. A material with extremely low moisture transmissivity, for example a metal or a polypropylene resin, is preferably employed for the housing 2.

The base 21 is formed with an insertion hole for inserting the sensor section 4, and an end portion 40 of the sensor section 4 is fixed at the inside face of the base 21. A bonding film 5 is provided on the outside face of the base 21. An adhesive tape is employed on both faces of the bonding film 5. The bonding film 5 is itself attached to the base 21 through the tape on one face, and the continuous glucose monitoring device 1 is attached to the skin 6 through the tape on the other face.

The circuit board 3 is equipped with electronic configuration elements required for overall control of the continuous glucose monitoring device 1. The circuit board 3 is configured including a connection portion 30 for making contact with an electrode 42 (see FIG. 2) of the sensor section 4, described later. The connection portion 30 is employed to apply a voltage to the sensor section 4 and obtain a response current.

The sensor section 4 obtains a response that depends on the glucose concentration in the blood or interstitial subcutaneous fluid. A first end portion 40 of the sensor section 4 makes contact with the connection portion 30 of the circuit board 3, and the second end portion of the sensor section 4 is inserted into the skin 6.

Figure 2:
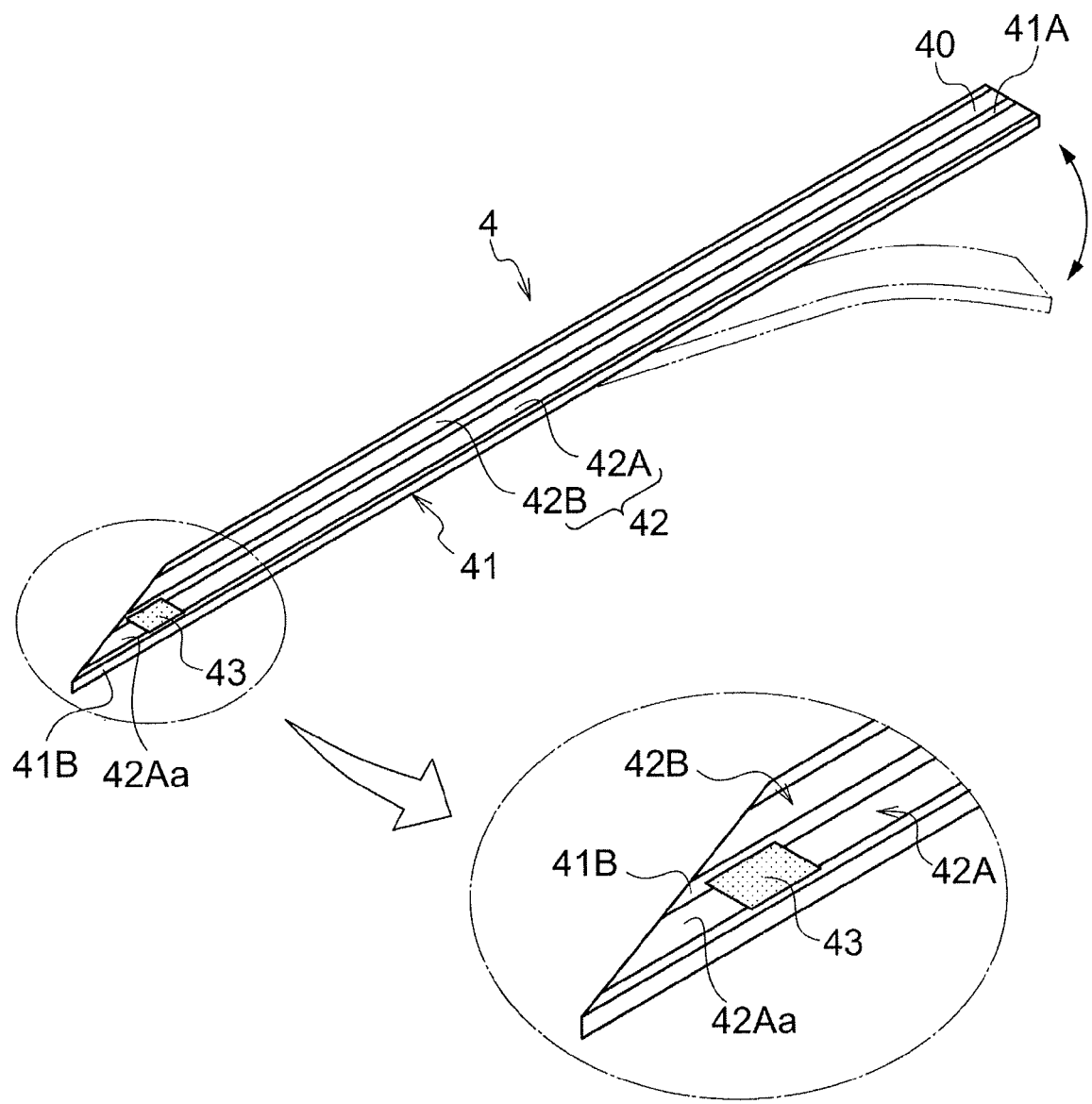
FIG. 2 is a perspective view of a sensor section with an enlarged diagram of a portion thereof.

As shown in FIG. 2, the sensor section 4 is configured including a base 41, the electrode 42 and an enzyme portion 43.

The base 41 is configured in sheet form from a flexible, electrically insulating material and supports the electrode 42. An end portion 41B of the base 41 on the side for insertion into the skin 6 is formed with a sharp profile, enabling the sensor section 4 to be easily inserted into the skin 6 and enabling pain of a user to be reduced. However, there are no particular limitations to the profile of the leading end of the base 41, and configuration may be made with a profile other than a sharpened profile. A material that has appropriate electrical insulating properties so as not to affect the human body can be employed as the material for the base 41, and, for example, a thermoplastic resin such as polyethylene terephthalate (PET), polypropylene (PP) or polyethylene (PE) may be employed therefor. A thermoset resin such as a polyimide resin or an epoxy resin may also be employed therefor.

The electrode 42 is configured including a working electrode portion 42A and a counter electrode portion 42B. By applying a voltage to the electrode 42 a current flows between the working electrode portion 42A and the counter electrode portion 42B corresponding to electrons extracted by the enzyme portion 43, described later.

The enzyme portion 43 acts to extract electrons from the glucose and pass the extracted electrons across to the working electrode portion 42A. The enzyme portion 43 can, for example, be a glucose oxidoreductase disposed on the working electrode portion 42A. A glucose oxidase (GOD) or a glucose dehydrogenase (GDH) can be employed as the glucose oxidoreductase. A known method can be employed as the method for affixing the glucose oxidoreductase, such as for example employing a method that uses a polymerizable gel, polyacrylamide, or a polymer such as phosphorus, a method that uses a MPC polymer of a phospholipid polymer coupled using a silane coupling agent, or a method using protein coating.

Figure 3:
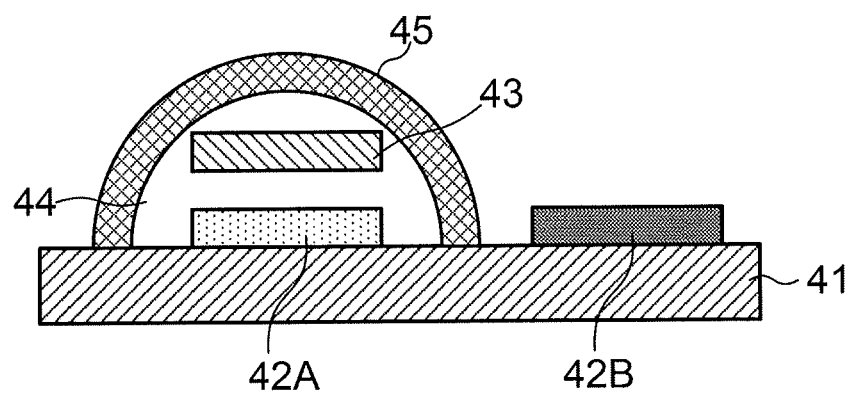
FIG. 3 is a cross-section illustrating an end portion (electrode portion) of a sensor section.

FIG. 3 schematically illustrates a cross-section configuration of the end portion 41B of the sensor section 4. The working electrode portion 42A and the counter electrode portion 42B are formed on the base 41, and a semi-permeable membrane 45 is formed so as to cover the working electrode portion 42A. The region configured by the base 41 and the semi-permeable membrane 45 is a reagent layer 44 and the enzyme portion 43 is disposed within the reagent layer 44. The enzyme portion 43 need not necessarily be affixed on the working electrode portion 42A, and configuration may be made such that the enzyme portion 43 is disposed within the reagent layer 44, above the working electrode portion 42A but not making contact with the working electrode portion 42A.

The semi-permeable membrane 45 is provided to prevent sensor sensitivity from becoming saturated immediately, for example to prevent sensitivity saturation to an upper limit of detectable concentration of glucose for the sensor, and the semi-permeable membrane 45 restricts passage of glucose to the enzyme portion 43. The semi-permeable membrane 45 also suppresses the passing through to the enzyme portion 43 of interfering substances that would impede reaction. A cellulose acetate membrane or polyurethane membrane may be employed as the semi-permeable membrane 45. In the present exemplary embodiment a case will be explained in which a cellulose acetate membrane is employed as the semi-permeable membrane 45 (referred to below as CA membrane). Note that the semi-permeable membrane 45 is one example of an external membrane in the present invention. However, the external membrane is not limited to materials having a property of restricting passage of glucose to the enzyme portion 43.

The method of forming the sensor section 4 is by, for example, forming the working electrode portion 42A and the counter electrode portion 42B on the base 41 by screen printing employing a carbon ink, covalent bonding a carbodiimide thereon, dripping a bridged glucose oxidoreductase thereon using glutaraldehyde (GA) as the bridging agent, and then drying with warm air at 40° C. for 15 minutes. Then a CA membrane can be formed as the semi-permeable membrane 45 using spin coating or dip coating so as to form a covering. Configuration may also be made with such compounds as a bis (sulphosuccinimidyl) suberate or bis-N-succinimidyl-(nonaethylene glycol) ester.

Figure 4:
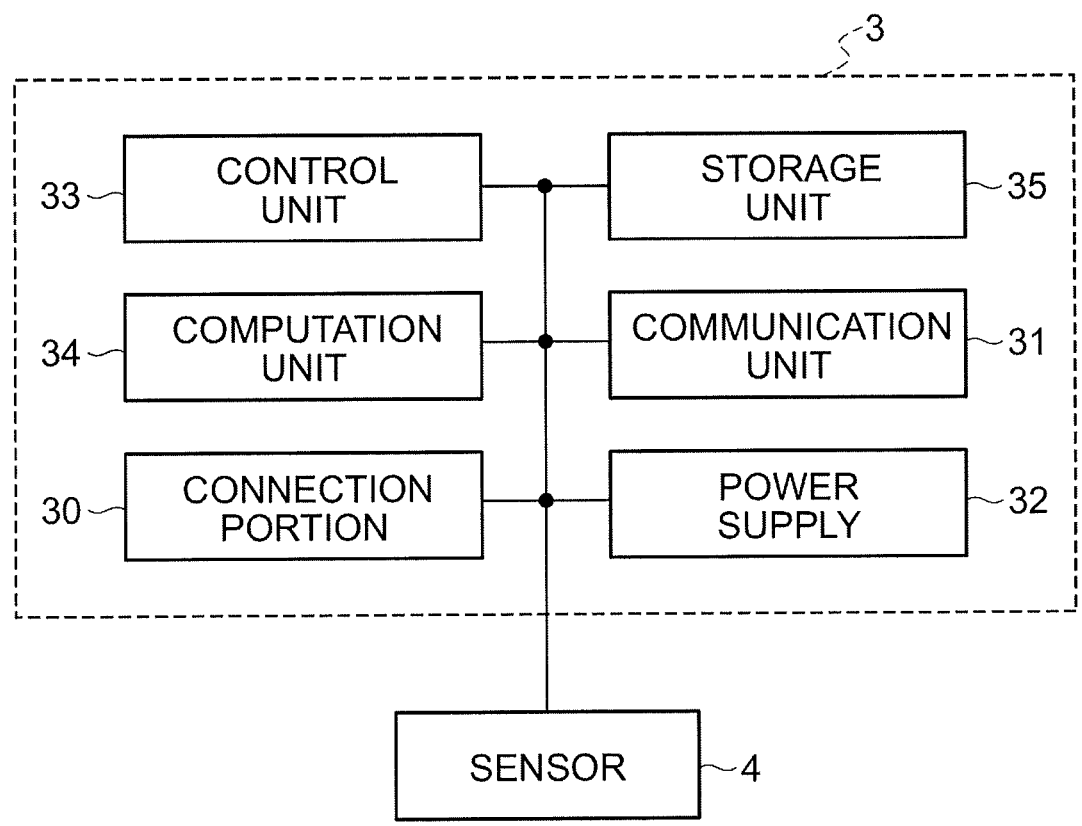
FIG. 4 is a block diagram illustrating a schematic configuration of a circuit board.

As shown in FIG. 4, the circuit board 3 is configured including the connection portion 30 and also a communication unit 31, a power supply 32, a control unit 33, a computation unit 34 and a storage unit 35.

The communication unit 31 performs data communication between the continuous glucose monitoring device 1 and an external data processing apparatus. The communication unit 31 is configured including at least a transmission unit, and as required also includes a reception unit. Data communication may be by means of, for example, wireless communication such as infrared communication or Bluetooth. Configuration may also be made such that wired data communication is performed, and in such cases a cable connecting portion is provided to the communication unit 31 of the continuous glucose monitoring device 1, such that data communication is performed by connecting with a cable to an external data processing apparatus, for example.

Examples of an external data processing apparatus include such an apparatus as an insulin supply device for administering insulin to a human body, a simple blood sugar measurement instrument, a wrist watch size display device, and a personal computer (PC).

In data communication between the continuous glucose monitoring device 1 and a simple blood sugar measurement instrument, for example, a blood sugar measurement result of the simple blood sugar measurement instrument can be transmitted to the continuous glucose monitoring device 1. The measurement result of the continuous glucose monitoring device 1 and the blood sugar measurement result received from the simple blood sugar measurement instrument can accordingly be compared, enabling correction of the measurement results of the continuous glucose monitoring device 1 to be performed. Configuration may be made such that the data (current values) measured by the continuous glucose monitoring device 1 are transmitted to the simple blood sugar measurement instrument such that the blood sugar values themselves are computed in the simple blood sugar measurement instrument.

In data communication between the continuous glucose monitoring device 1 and a wrist watch size display device, for example, the measurement result of the continuous glucose monitoring device 1 can be transmitted to the wrist watch size display device. Such an approach enables a user to easily ascertain the measurement results even when the continuous glucose monitoring device 1 is mounted to a location that is difficult for a user to see, such as a user's shoulder or abdominal region.

Data communication between the continuous glucose monitoring device 1 and a PC, for example, enables the data (current values) measured by the continuous glucose monitoring device 1 to be transmitted to the PC. The glucose concentration trend can be displayed and various analyses can then be performed by the PC. Configuration may be made such that correction data or the like is transmitted from a PC to the continuous glucose monitoring device 1.

The power supply 32 is a direct current power source for supplying power to the circuit board 3 and the sensor section 4, and a battery with a 1 to 3V power supply voltage can be employed, for example.

The control unit 33 controls the continuous glucose monitoring device 1 overall, controlling, for example, such aspects as the voltage application timing, response current sampling, glucose concentration computation processing and communication to an external data processing apparatus.

The computation unit 34 executes various computations required in processing in the continuous glucose monitoring device 1, including for example computation of the glucose concentration.

Programs, such as a program for executing a testing mode processing routine, described later, various programs for execution by the control unit 33, and data such as a correction curve, correction data and voltage application patterns employed in computations of the computation unit 34 are stored in the storage unit 35. The response current detected by the sensor section 4 and the glucose concentration data computed by the computation unit 34 are also stored in the storage unit 35.

The control unit 33, the computation unit 34 and the storage unit 35 may be configured by electrical components such as a CPU and/or an MPU, ROM and RAM mounted on the circuit board 3.

Figure 5:
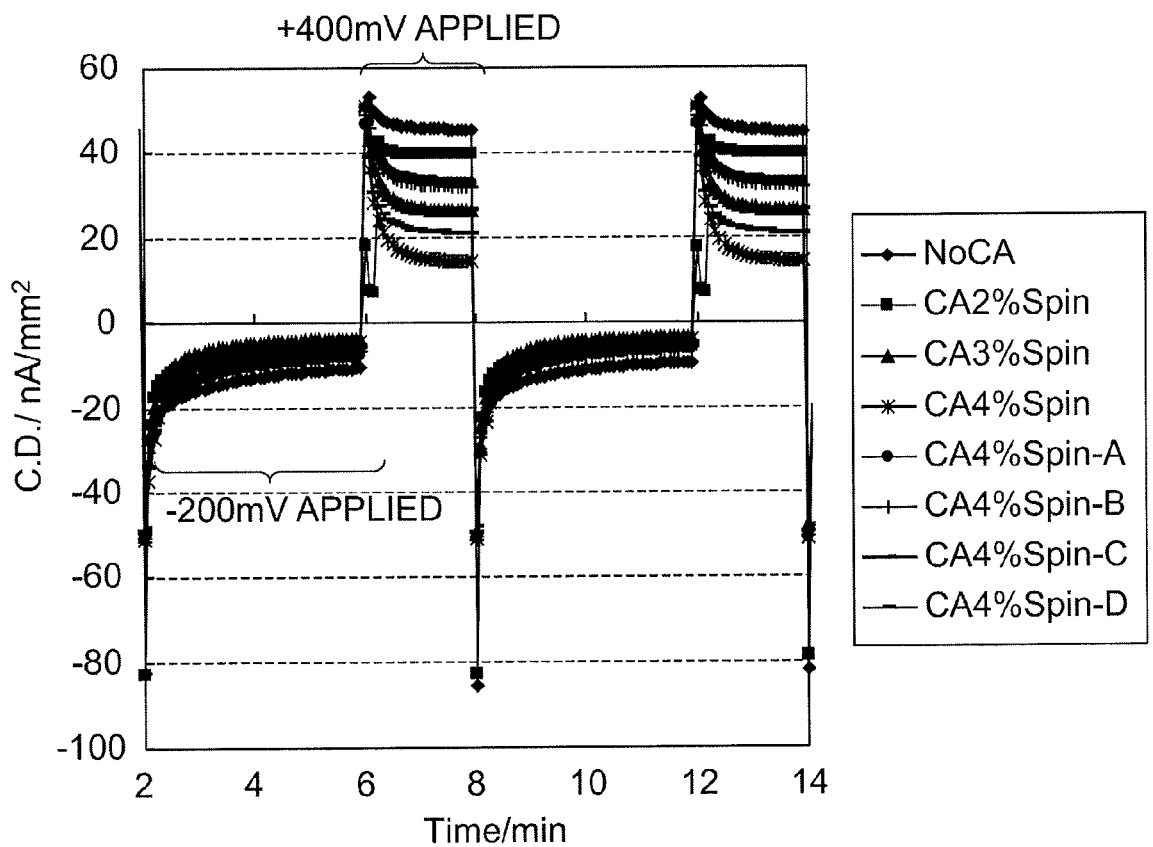
FIG. 5 is a graph illustrating response current when a response voltage has been applied.

In the thus configured continuous glucose monitoring device 1 of the present exemplary embodiment, in a monitoring mode the response current is measured when a predetermined voltage pattern, such as illustrated in FIG. 5, is applied. In the testing mode the state of the sensor section 4, and in particular the state of the semi-permeable membrane 45, is tested based on changes in response current when a voltage that obtains a response caused by glucose is applied.

Explanation follows regarding the principles of the testing mode in the continuous glucose monitoring device 1 of the first exemplary embodiment.

For example, the voltage pattern illustrated in FIG. 5 is a pattern in which a voltage that does not obtain a response caused by glucose (referred to below as non-response voltage E1) is applied for a specific period of time (−200 mV for 240 seconds in this example), followed by application of a voltage that obtains a response caused by glucose (referred to below as response voltage E2) for a specific period of time (400 mV for 120 seconds in this example). The testing mode in the first exemplary embodiment utilizes the amount of change in response current from immediately after application of the response voltage E2.

The non-response voltage E1 is a voltage to which glucose does not respond at all or a voltage to which glucose exhibits a slight response, but at a level which in practice can be considered as no response. More precisely, the response current when the non-response voltage E1 is applied to the sensor section 4 includes extremely small responses caused by glucose, but is mainly caused by external environmental background factors such as background due to the particularities of the sensor, and background and noise of co-present substances. The magnitude of the non-response voltage E1 is set based on the specification of the sensor section 4 (for example according to factors such as the amount of enzyme used, the method of affixing the enzyme, the material of the electrodes and the response region). More specifically, the non-response voltage E1 is set in a range of −0.5V to +0.5V (preferably −25 mV to +25 mV) from the response initiation voltage at which the response current caused by glucose starts to flow when the voltage applied to the sensor section 4 is increased.

The response voltage E2 is a voltage at which glucose exhibits sufficient response. The magnitude of the response voltage E2 is set based on the specification of the sensor section 4 (for example factors such as the amount of enzyme used, the method of affixing the enzyme, the material of the electrodes and the response region).

Figure 6:
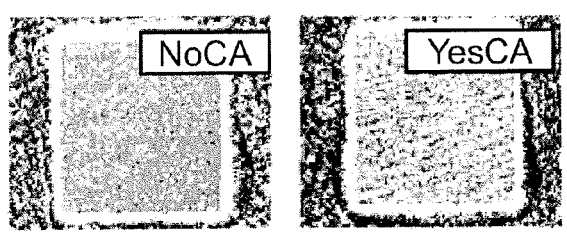
FIG. 6 shows images of states of CA membranes of a sensor section.
Figure 6:
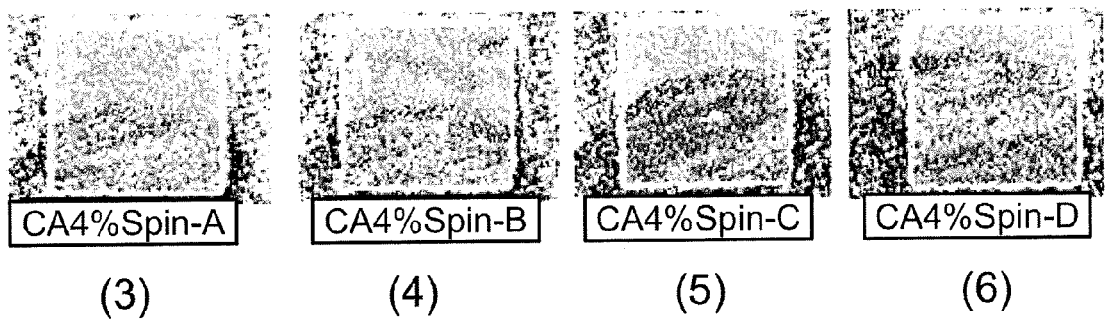

FIG. 5 illustrates response currents when such a voltage pattern is applied to plural sensors with different states of semi-permeable membrane 45 (CA membrane). The glucose concentration is 100 mg/dL. The states of the CA membranes of each of the respective plural sensors are, as shown in FIG. 6, (1) no CA membrane (NoCA), (2) with CA membrane (YesCA), and (3) through (6) simulated defective membranes with 4% concentration CA membrane only covering a portion of the sensor section 4 (CA4% Spin-A to -D). For FIG. 6 (3) through (6), the dark portions at the lower part of the figure are the parts covered by the CA membrane. The defect ratio for each sensor (a proportion of an area that is not covered by the CA membrane with respect to the area of the sensor section) is, respectively, (1) 100 percent, (2) 0 percent, (3) 65 percent, (4) 64 percent, (5) 35 percent, and (6) 10 percent. Moreover, for (2) with CA membrane (YesCA), CA membrane examples concentrations of 2% (CA2% Spin), 3% (CA3% Spin) and 4% (CA4% Spin) are prepared. Due to the difficulties in actually measuring the membrane thickness of the CA membrane the membrane thickness of the CA membranes are indicated by concentrations of the membranes.

Figure 7:
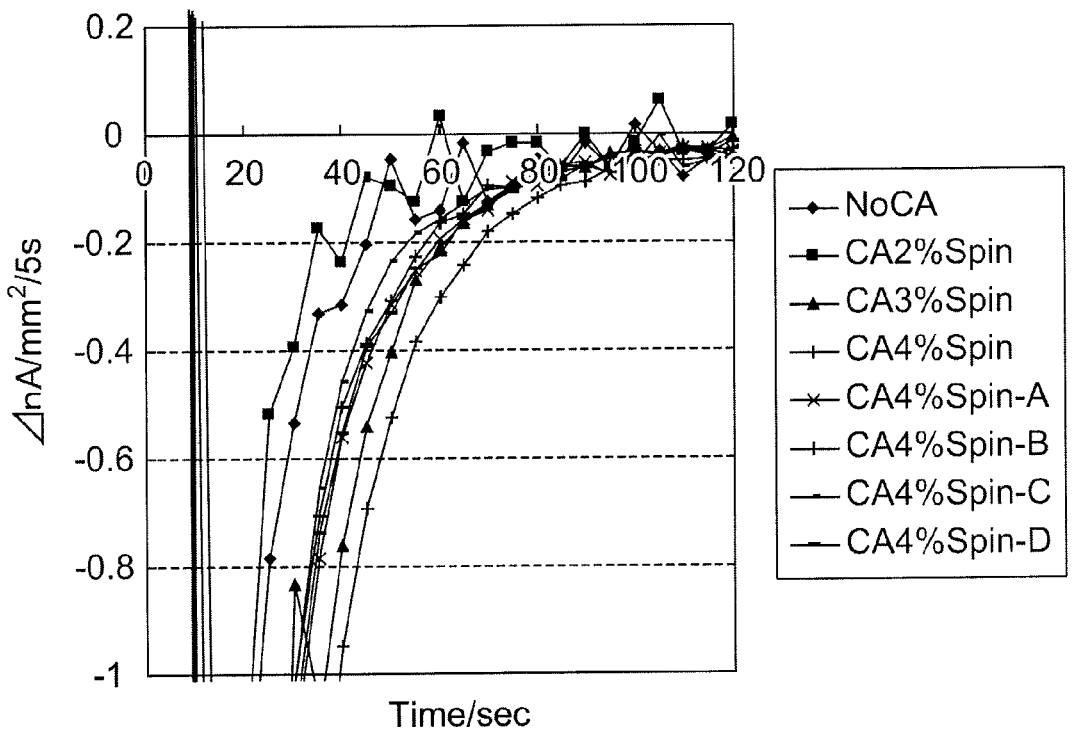
FIG. 7 is a graph illustrating changes in response current after application of a response voltage.
Figure 8:
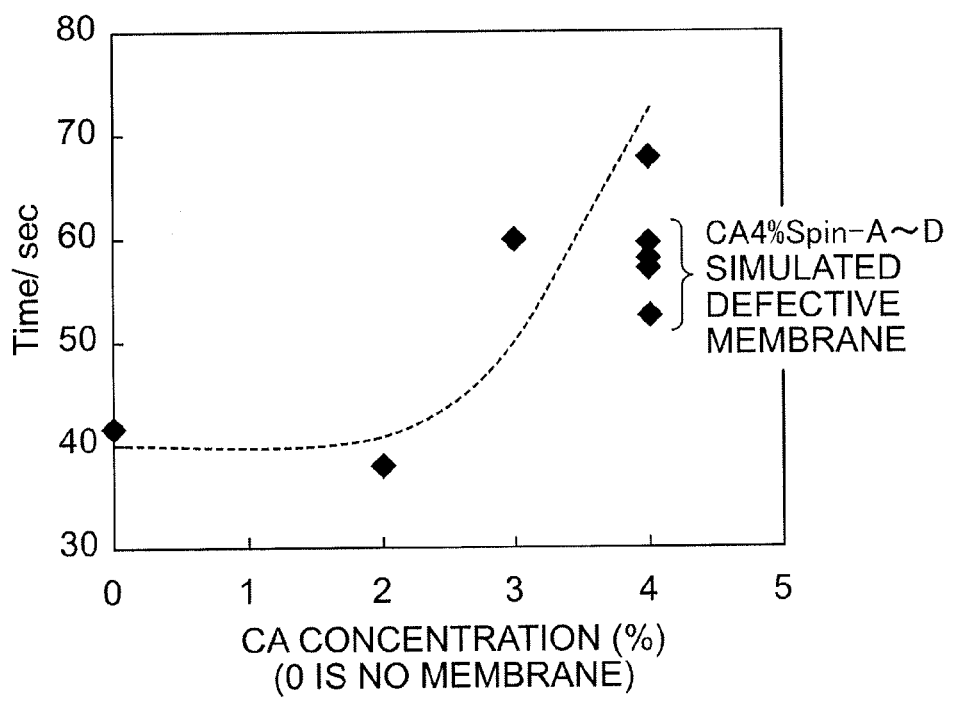
FIG. 8 is a graph illustrating the time until the amount of change of the response current becomes less than a change amount threshold value for each sensor with a different CA membrane state when a response voltage has been applied.

The amount of change in the response current from immediately after application of the response voltage E2 (+400 mV) for each of the sensors is illustrated in FIG. 7. The sampling interval employed is 5 seconds. A graph illustrating the time until the absolute values of the amount of change in response current every 5 seconds $\Delta nA/mm^2/5$ s becomes smaller than specific change amount threshold values (here, set at 0.2 $nA/mm^2$) are shown in FIG. 8. As seen from these graphs, the period of time until the change in response current becomes small is earlier for thinner membrane thickness sensors CA3% Spin and CA2% Spin than for the thickest sensor CA4% Spin. The cause of this difference in time is postulated to be due to response delay based on the glucose permeability restriction by the CA membrane. Moreover, the time until the change of the response current becomes smaller is earlier in the sensors with simulated defective membranes CA4% Spin-A to -D than in the CA4% Spin sensor with completely covered surface.

Taking a normal state as a CA4% Spin sensor, by utilizing these results it is possible to ascertain a state in which the membrane thickness of the CA membrane has become thinned, and a state in which a portion of the CA membrane has been damaged, at the manufacturing stage or during use. In this case the change amount threshold value is 0.2 $nA/mm^2$, however the change amount threshold values are appropriately set according to such factors as the specification of the sensor section 4 and the sampling periods.

Figure 9:
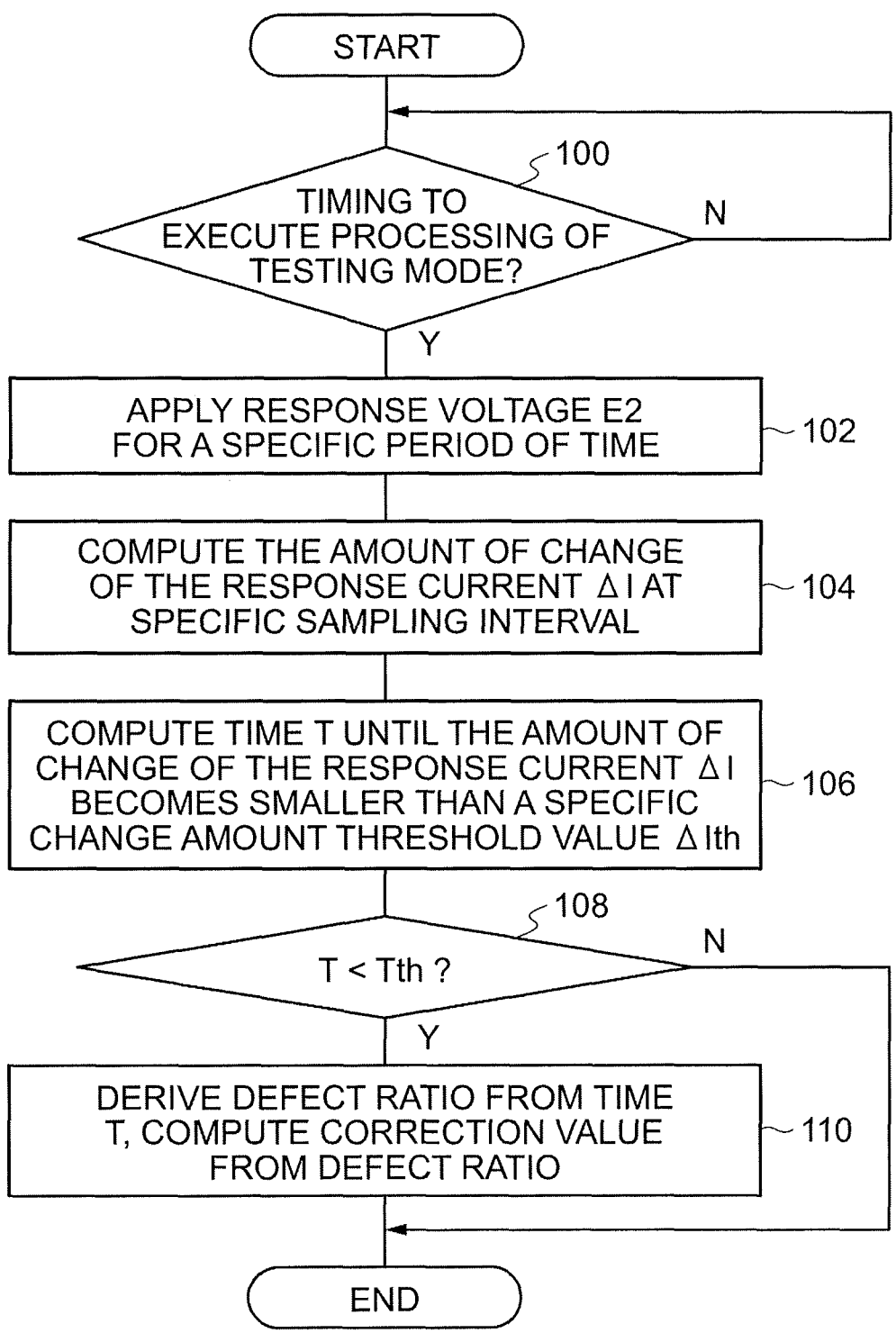
FIG. 9 is a flow chart illustrating a testing mode processing routine executed in a continuous glucose monitoring device of a first exemplary embodiment.

Explanation follows regarding a testing mode processing routine executed during the testing mode of the continuous glucose monitoring device 1 of the first exemplary embodiment, with reference to FIG. 9.

At step 100 determination is made as to whether or not it is a timing for executing the processing of the testing mode. For example configuration may be determined such that the testing mode is executed every hour, or executed at predetermined times, and determination at this step is whether or not such a time has arrived. Configuration may also be made such that the execution timing of the testing mode is determined to be in the night time when there will be little influence on continuous monitoring. Configuration may also be made such that immediately after starting to use the continuous glucose monitoring device 1 the timing of testing mode execution is determined, for example so as to be executed on the seventh day from start of use, when no rapid change in the state of the sensor is anticipated. Processing transitions to step 102 when determined that the execution timing for the testing mode has arrived. However when determined that the execution timing for the testing mode has not yet arrived determination at step 100 is repeated until determined that the execution timing has arrived.

In step 102 the response voltage E2 is applied. For example a voltage of +400 mV is applied for 120 seconds. Then, in step 104, at a specific sampling interval (for example 5 seconds), the amount of change of the response current ΔI is measured. Then at step 106, with the timing at which the response voltage E2 is applied at step 102 as a starting point, the time T until the measured amount of change of the response current ΔI becomes smaller than a specific change amount threshold value ΔIth in the specific period of time when the response voltage E2 is applied is computed. Note that explanation is made of a case in which the amount of change of the response current ΔI is an absolute value. However, it is not limited to an absolute value, and the actual value may be employed. In such a case, the time T until the amount of change of the response current ΔI becomes larger than a specific change amount threshold value ΔIth is computed. In other words, the time T until the amount of change of the response current ΔI reaches a value in a specific range can be computed.

Then at step 108, comparison is made of the time T computed at step 106 and a time threshold value Tth and determination is made as to whether or not the time T is smaller than the time threshold value Tth. The time threshold value Tth is set with reference to the time when the response voltage E2 is applied until the amount of change of the response current ΔI becomes smaller than the change amount threshold value ΔIth for a case when a sensor with normal semi-permeable membrane 45 is employed. For example, as shown in FIG. 8, with CA4% Spin as a normal sensor, the time threshold value Tth can be set at 70±α seconds where α can be between 5 to 20 seconds. When time T<time threshold value Tth, determination is made that the state of the semi-permeable membrane 45 has changed, namely that a defect has occurred, and processing transitions to step 110. However, when time T≥time threshold value Tth, determination is made that the state of the semi-permeable membrane 45 has not changed, that is, the semi-permeable membrane 45 is in a normal state, and the processing is ended.

At step 110, the defect ratio of the semi-permeable membrane 45 is derived based on the time T computed at step 106. Then, a correction value for the response current to be measured in the monitoring mode corrected according to the defect ratio is computed and stored in the storage unit 35.

Figure 10:
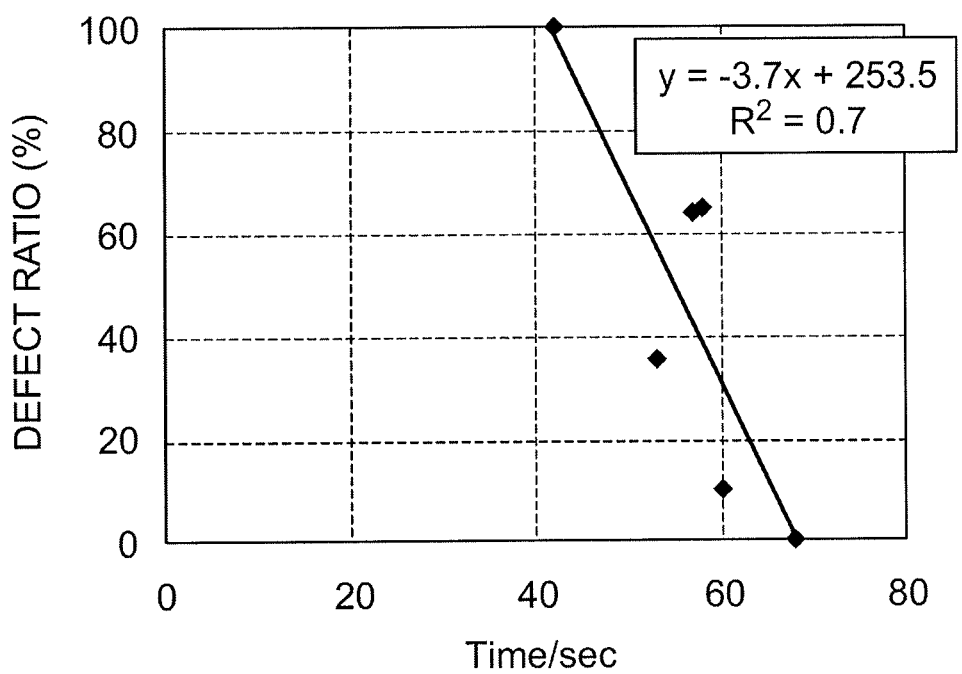
FIG. 10 is a graph illustrating a relationship between the time until the amount of change of the response current becomes less than a change amount threshold value with respect to a defect ratio when a response voltage has been applied.

More specifically, first the relationship between the time T and the defect ratio is plotted, as shown in FIG. 10. For instance, for each of the sensors shown in FIG. 6, the times T in the case the change amount threshold value ΔIth is set at 0.2 nA/mm² are computed, and the relationship between the times T and the defect ratios for each of the sensors are plotted on a graph with the horizontal axis as time T and the vertical axis as the defect ratio. Moreover, the defect ratio may be taken as the proportion the membrane thickness (concentration) of the CA membrane of the sensor is smaller with respect to the membrane thickness (concentration) of the CA membrane of a normal sensor. A correspondence between the plotted time T and the defect ratio is derived and pre-stored in the storage unit 35. The correspondence of the time T to the defect ratio is then employed to derive the defect ratio corresponding to a time T computed at step 106. For example, in the example of FIG. 10, if the time T is 60 seconds then the defect ratio is derived as 31.5%.

Figure 11A:
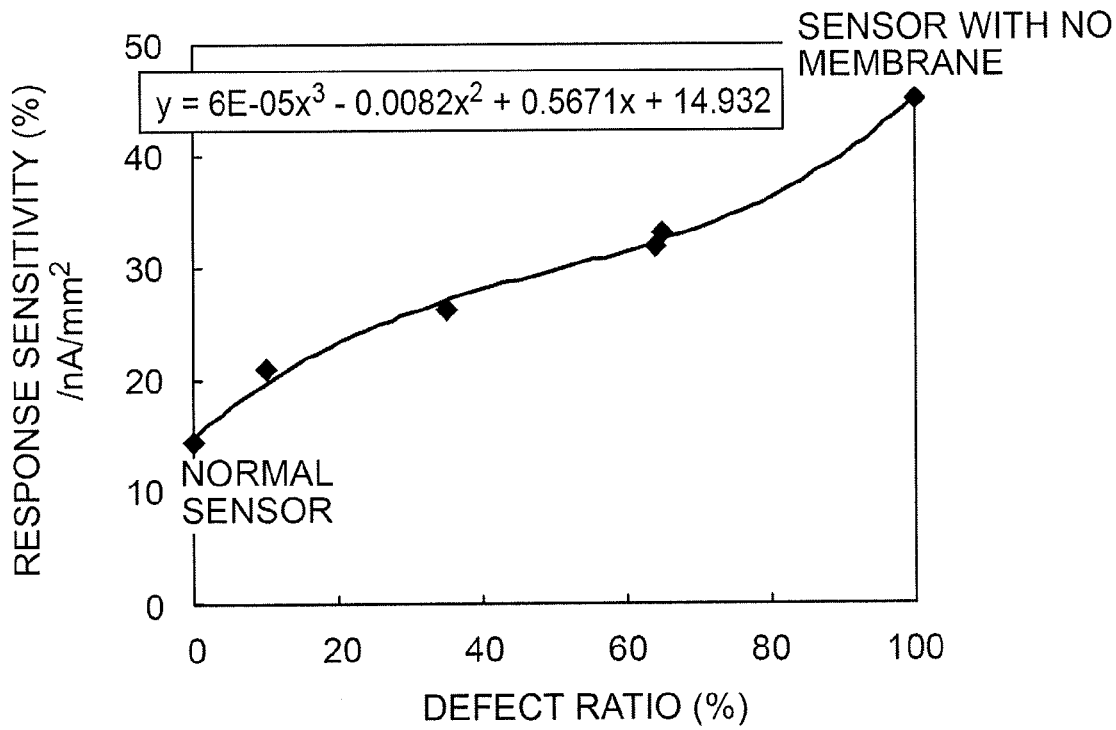
FIG. 11A and FIG. 11B are graphs illustrating relationships between a defect ratio with respect to a sensitivity normal-error difference.
Figure 11B:
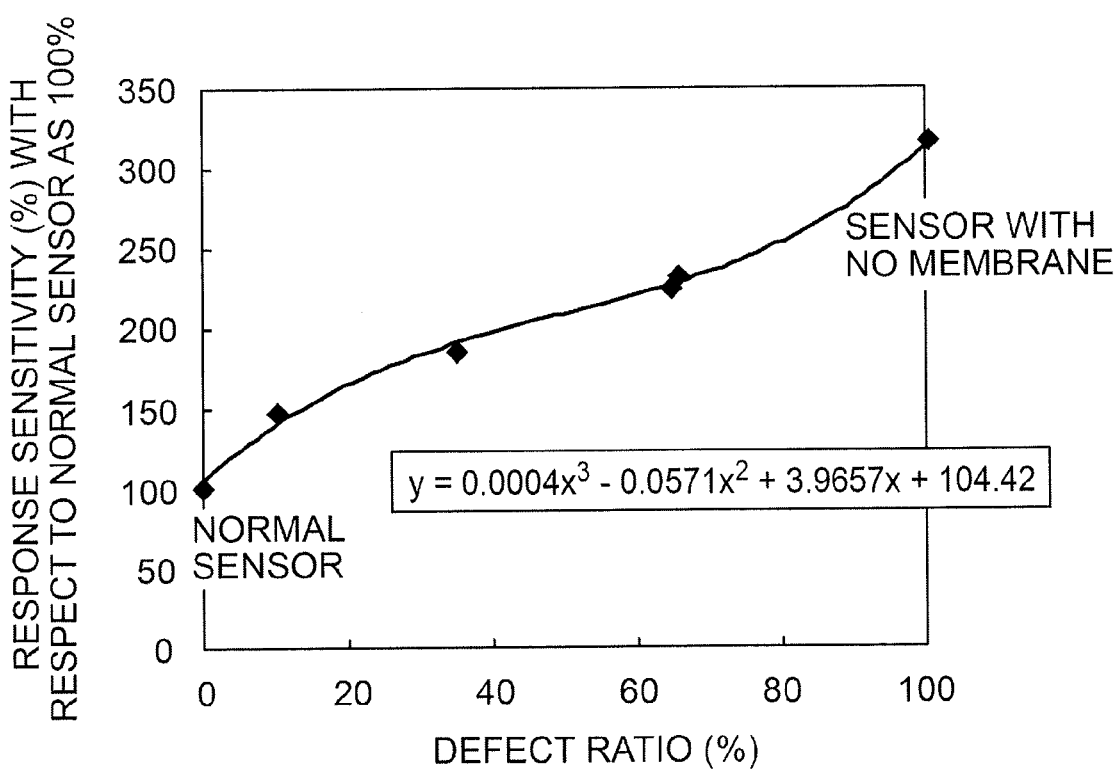

Here, FIG. 11A shows the relationship between the response current sensitivity obtained 100 seconds after applying the response voltage E2 with respect to the defect ratios of the CA membranes (1) through (6) shown in FIG. 6. Note that obtaining the response current sensitivity is not limited to this timing and the response current sensitivity can be obtained at any timing within the range in which there is a discernable amount of response current sensitivity. Then, for example as shown in FIG. 11B, the relationship between the defect ratio and a sensitivity normal-error difference of the sensor is plotted. The sensitivity normal-error difference is indicated as a proportion with normal response sensitivity taken as 100. Depending on the defect ratio there is a % increase compared to a normal sensor for the point at which determination can be made of whether or not response current is output. The correspondence between the plotted defect ratio and the sensitivity normal-error difference is derived and pre-stored in the storage unit 35. Then the correspondence between the defect ratio and the sensitivity normal-error difference is employed to derive the sensitivity normal-error difference corresponding to the derived defect ratio. For example in the example of FIG. 11, when the defect ratio is 31.5% a sensitivity normal-error difference of about 185.2% is derived. This sensitivity normal-error difference is then stored in the storage unit 35 and processing ended.

In the monitoring mode the response current values actually measured are corrected, for example to a measured value/correction value using the above correction value, with this then output as the measurement result.

As explained above, according to the continuous glucose monitoring device of the first exemplary embodiment, the time employed to test the state of the semi-permeable membrane is the time until the amount of change of the response current immediately after a voltage that obtains a response caused by glucose is applied becomes less than a predetermined change amount threshold value. Hence sensor state testing can be performed stably and in a short time without providing plural sets of working electrodes and counter electrodes. In particular, since the change in response current immediately after voltage application is employed for testing, the execution time for the testing mode can be made shorter than in cases employing the time until the response current reaches a steady state. This is more efficient in cases such as the present exemplary embodiment in which continuous monitoring is performed. In the first exemplary embodiment, explanation is given of a case in which a defect in a sensor is determined based on the time T until the amount of change of the response current ΔI when the response voltage E2 is applied (the first voltage) becomes smaller than a change amount threshold value ΔIth. However, configuration may be made in which the time T until the amount of change of the response current ΔI when a non-response voltage E1 is applied reaches a value within a specific range is used.

Second Exemplary Embodiment

Next, the second exemplary embodiment is explained. The second exemplary embodiment differs from the first exemplary embodiment in that the defect ratio of the sensor is determined based on the amount of change of the response current ΔI itself after the response voltage E2 is applied. Note that the configuration of the continuous glucose monitoring device 1 of the second exemplary embodiment is the same as the continuous glucose monitoring device 1 of the first exemplary embodiment. Hence, the explanation thereof is omitted.

Hereafter, explanation will be made of the principles of the testing mode in the continuous glucose monitoring device 1 of the second exemplary embodiment.

Figure 12:
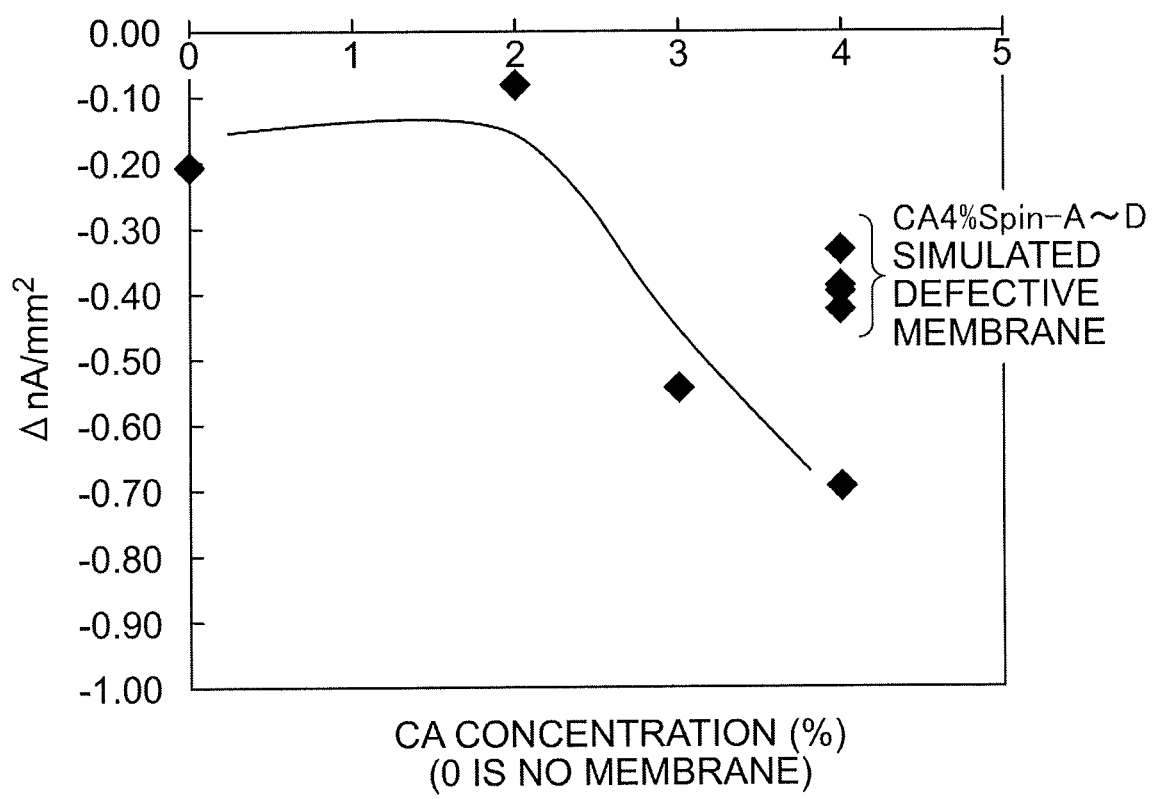
FIG. 12 is a graph illustrating the amount of change of the response current for each sensor with a different CA membrane state, when a response voltage has been applied.

As in the first exemplary embodiment, the amount of change in the response current a predetermined period (here, 40 seconds) after application of the response voltage E2 (+400 mV) using each of the sensors shown in FIG. 6 is illustrated in FIG. 12. As seen from FIG. 12, the change in response current is larger for thinner membrane thickness sensors CA3% Spin and CA2% Spin than for the thickest sensor CA4% Spin. The cause of this is postulated to be due to response delay based on the glucose permeability restriction by the CA membrane. Moreover, the change of the response current is larger in the sensors with simulated defective membranes CA4% Spin-A to -D than in the CA4% Spin sensor with completely covered surface.

Taking a normal state as a CA4% Spin sensor, by utilizing these results it is possible to ascertain, a state in which the membrane thickness of the CA membrane has become thinned and a state in which a portion of the CA membrane has been damaged, at the manufacturing stage or during use.

Figure 13:
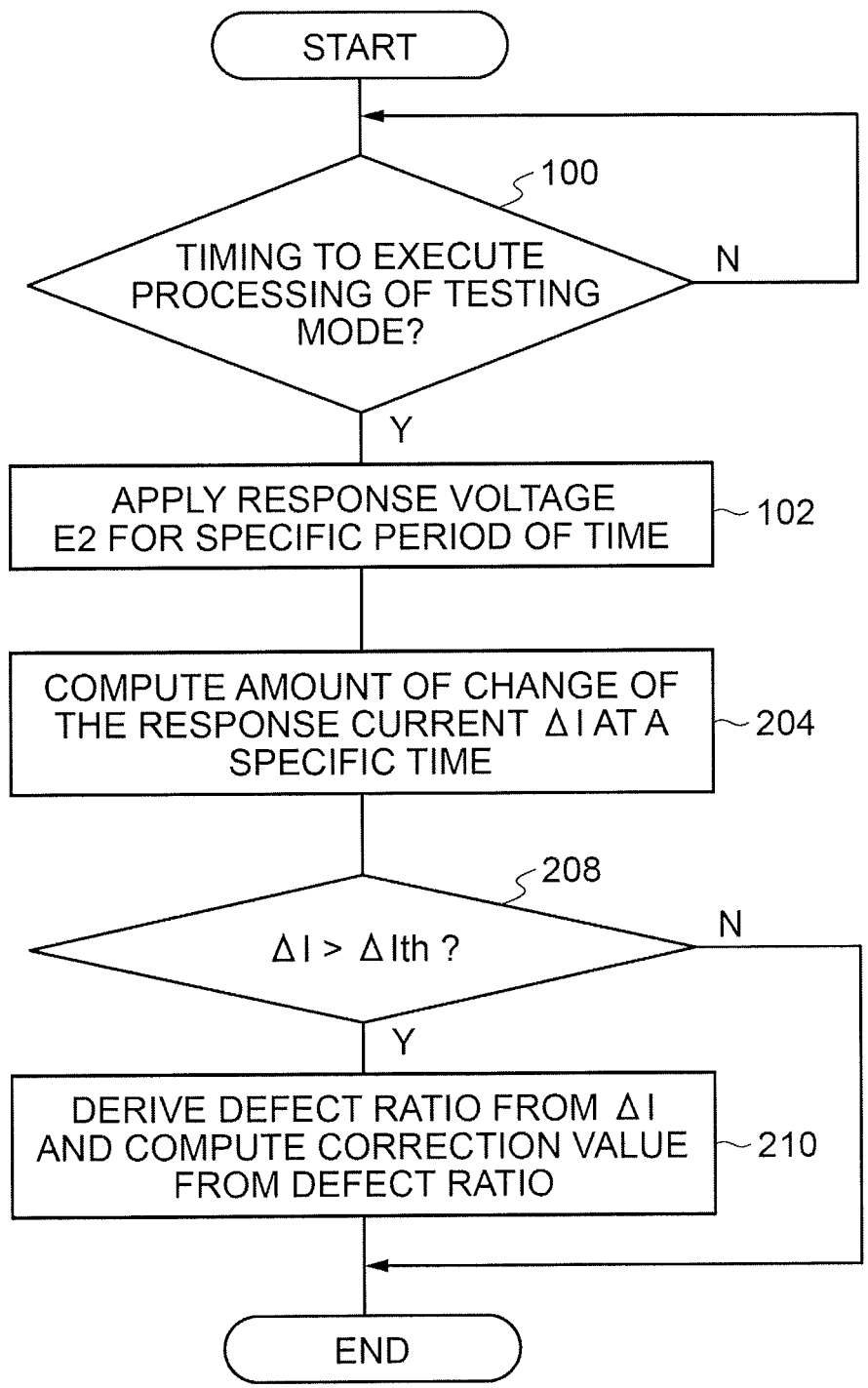
FIG. 13 is a flow chart illustrating a testing mode processing routine executed in a continuous glucose monitoring device of a second exemplary embodiment.

Explanation follows regarding a testing mode processing routine executed during the testing mode of the continuous glucose monitoring device 1 of the second exemplary embodiment, with reference to FIG. 13. Note that the same processing in the testing mode processing routine of the first exemplary embodiments is given the same reference numeral and the explanation thereof is omitted.

At step 100 determination is made as to whether or not it is a timing for executing the processing of the testing mode. Processing transitions to step 102 when determined that the execution timing for the testing mode has arrived. However, when determined that the execution timing for the testing mode has not yet arrived, determination at step 100 is repeated until determined that the execution timing has arrived.

In step 102 the response voltage E2 is applied for a specific length of time. For example a voltage of +400 mV is applied for 40 seconds. Then at step 204, with the timing at which the response voltage E2 is applied in step 102 as a starting point, the amount of change of the response current ΔI is measured at a specific time thereafter.

Then at step 208, determination is made as to whether or not the amount of change of the response current ΔI measured in step 204 is larger than a specific change amount threshold value. When it is determined that ΔI>change amount threshold value ΔIth, the state of the semi-permeable membrane 45 is determined to have changed, namely that a defect has occurred, and processing transitions to step 210. However, when it is determined that ΔI≤change amount threshold value ΔIth, the state of the semi-permeable membrane 45 is determined not to have changed, that is, the semi-permeable membrane 45 is in a normal state, and the processing is ended. Note that explanation is made of a case in which the amount of change of the response current ΔI is an actual value. However, it is not limited to this, and an absolute value may be employed. In such a case, determination is made as to whether or not the amount of change of the response current ΔI becomes smaller than a specific change amount threshold value ΔIth.

At step 210, the defect ratio of the semi-permeable membrane 45 is derived based on the amount of change of the response current ΔI computed at step 204. Then, a correction value for the response current to be measured in the monitoring mode corrected according to the defect ratio is computed and stored in the storage unit 35.

Figure 14:
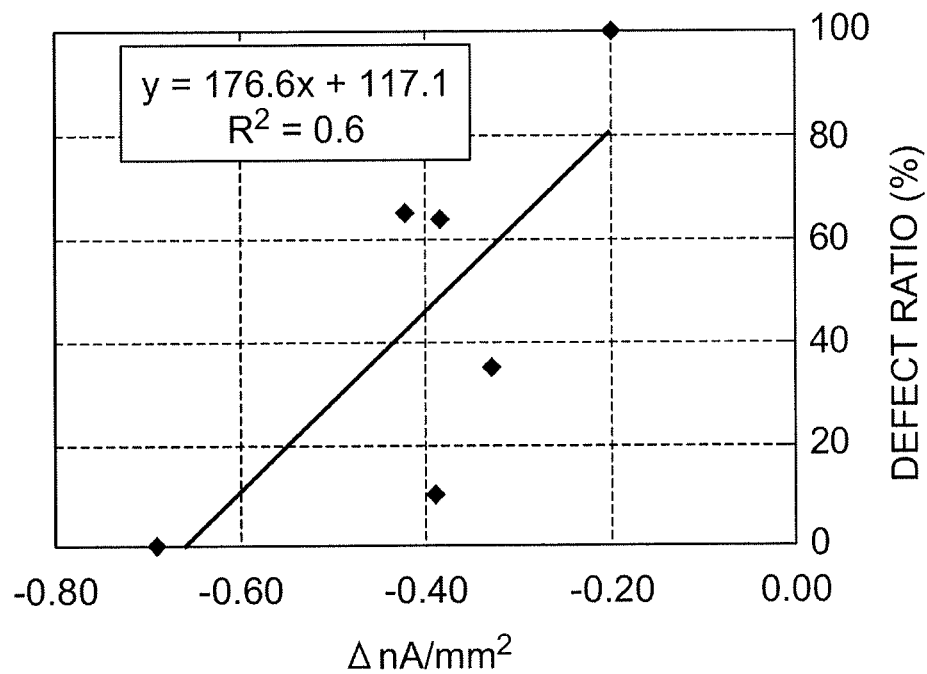
FIG. 14 is a graph illustrating a relationship between the amount of change of the response current with respect to a defect ratio when a response voltage has been applied.

More specifically, first the relationship between the amount of change of the response current ΔI and the defect ratio is plotted, as shown in FIG. 14. For instance, for each of the sensors shown in FIG. 6, the change amount threshold value ΔIth is set at −0.2 nA/mm$^2$, and the relationship between the amount of change of the response current ΔI and the defect ratio for each sensor is plotted on a graph with the horizontal axis as representing the amount of change of the response current ΔI and the vertical axis as representing the defect ratio. A correspondence between the amount of change of the response current ΔI and the defect ratio is derived and pre-stored in the storage unit 35. The correspondence of the amount of change of the response current ΔI to the defect ratio is then employed to derive the defect ratio corresponding to the amount of change of the response current ΔI measured at step 204. Then, as in the first exemplary embodiment, the derived relationship between the defect ratio and the sensitivity normal-error difference is employed to derive the sensitivity normal-error difference corresponding to the derived defect ratio.

As explained above, according to the continuous glucose monitoring device of the second exemplary embodiment, the amount of change of the response current at a specific time after an immediate application of a voltage that obtains a response caused by glucose is used to test the state of the semi-permeable membrane. Hence sensor state testing can be performed stably and in a short time without providing plural sets of working electrodes and counter electrodes. In particular, since the change in response current immediately after voltage application is employed for testing, the execution time for the testing mode can be made shorter than in cases employing the time until the response current reaches a steady state. This is more efficient in cases such as the present exemplary embodiment in which continuous monitoring is performed.

In the second exemplary embodiment, explanation is given of a case in which a defect in a sensor is determined based on the amount of change of the response current ΔI when the response voltage E2 is applied (the first voltage). However, configuration may be made in which the amount of change of the response current ΔI when a non-response voltage E1 is applied is used.

Third Exemplary Embodiment

Next, the third exemplary embodiment is explained. The third exemplary embodiment differs from the first exemplary embodiment in that the defect ratio of the sensor is determined based on both of the times T after the response voltage E2 and the non-response voltage E1 are applied. Note that the configuration of the continuous glucose monitoring device 1 of the third exemplary embodiment is the same as the continuous glucose monitoring device 1 of the first exemplary embodiment. Hence, the explanation thereof is omitted.

In the continuous glucose monitoring device 1 of the third exemplary embodiment, in a monitoring mode the response current is measured when a predetermined voltage pattern, such as illustrated in FIG. 5, is applied. In the testing mode the state of the sensor section 4, and in particular the state of the semi-permeable membrane 45, is tested based on changes in response current when a voltage that obtains a response caused by glucose is applied, and on changes to the response current when a voltage that does not obtain a response caused by glucose is applied.

Explanation follows regarding the principles of the testing mode in the continuous glucose monitoring device 1 of the third exemplary embodiment.

Figure 15A:
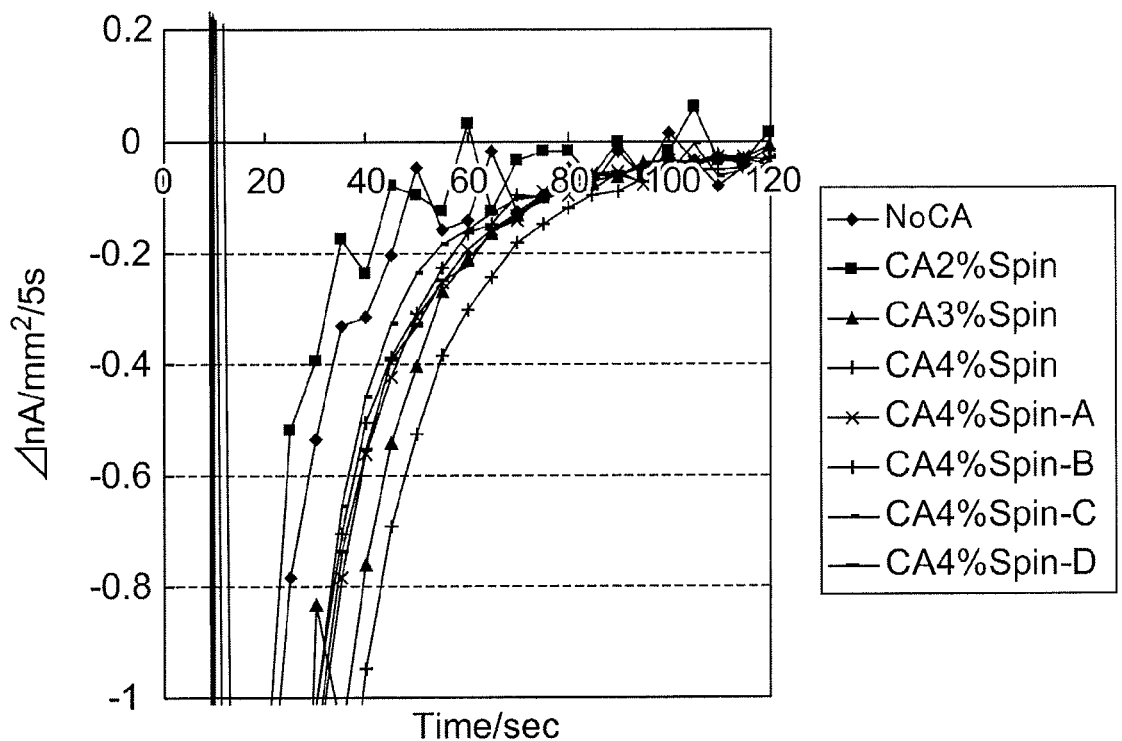
FIG. 15A is a graph illustrating changes in response current after application of a response voltage and FIG. 15B is a graph illustrating changes in response current after application of a non-response voltage.
Figure 15B:
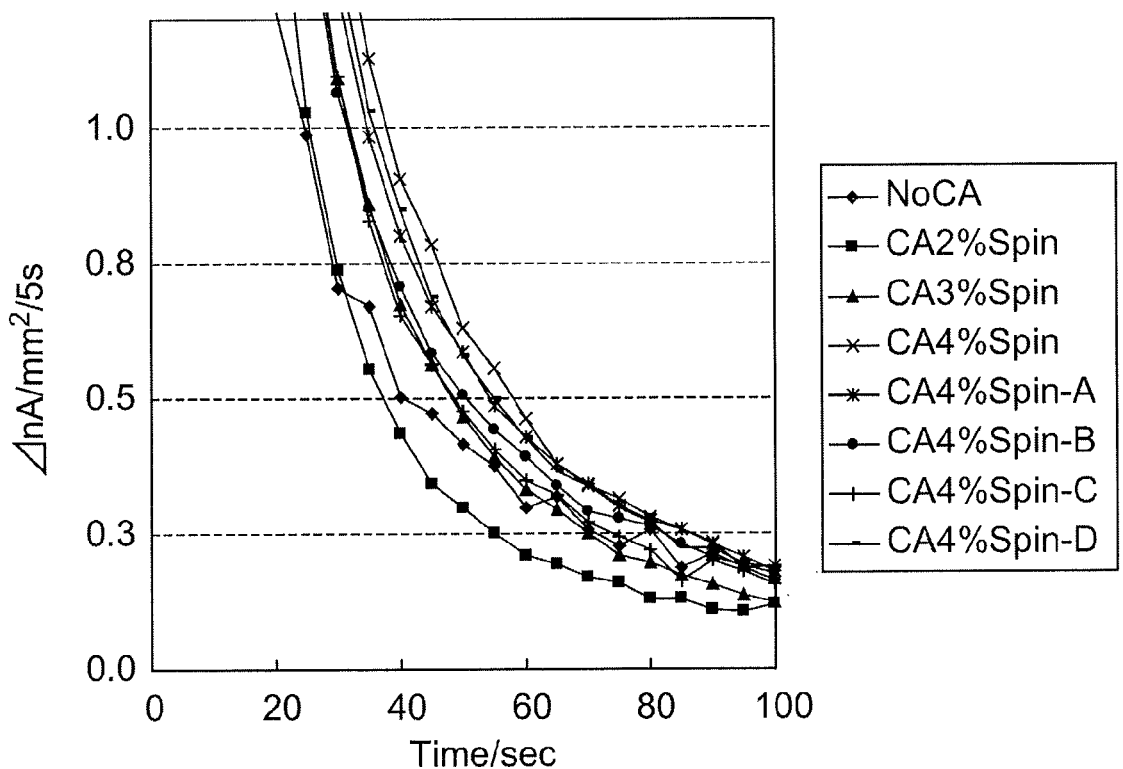
Figure 16A:
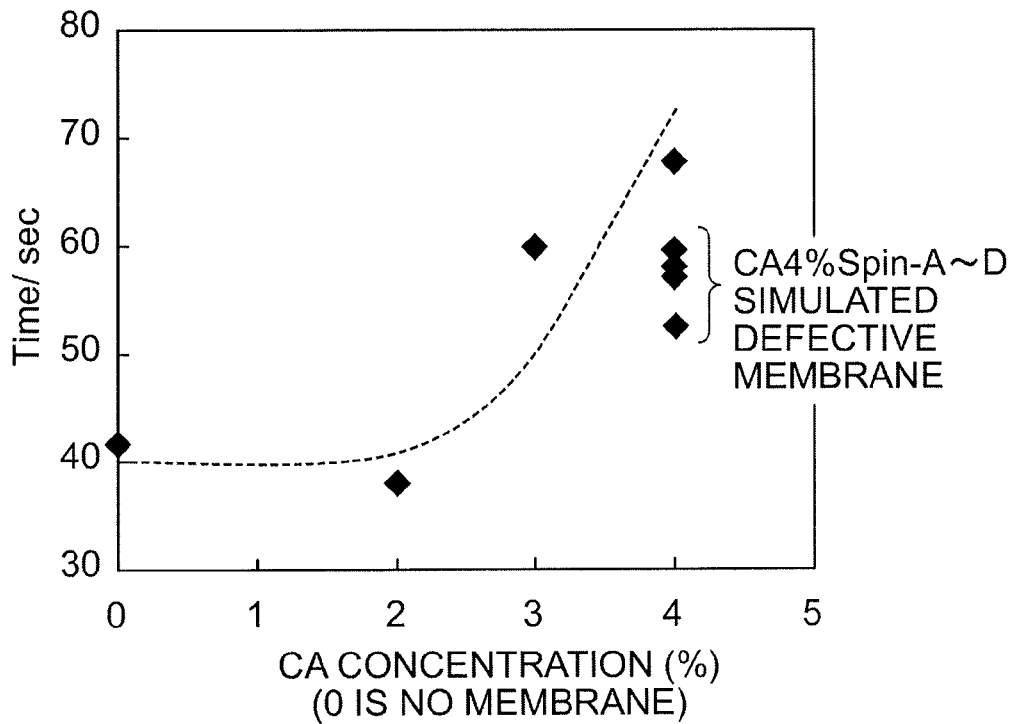
FIG. 16A and FIG. 16B are graphs illustrating the time until the amount of change of the response current becomes less than a change amount threshold value for each sensor with a different CA membrane state when a response voltage has been applied, with FIG. 16A illustrating when a response voltage has been applied and FIG. 16B illustrating when a non-response voltage has been applied.
Figure 16B:
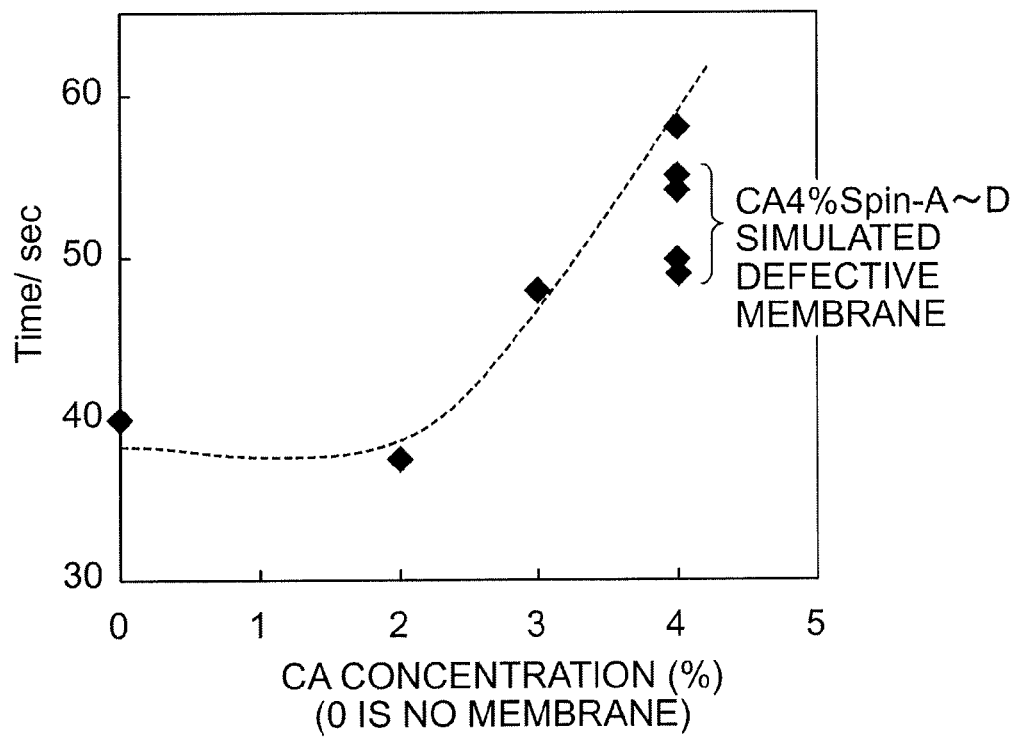

As in the first exemplary embodiment, the amount of change in the response current from immediately after application of the response voltage E2 (+400 mV) for each of the sensors shown in FIG. 6 is illustrated in FIG. 15A. The amount of change in the response current of the non-response voltage E1 (−200 mV) for each of the sensors is illustrated in FIG. 15B. Note that FIG. 15A is the same as FIG. 7. The sampling interval employed is 5 seconds. Graphs illustrating the time until the absolute values of the amount of change in response current every 5 seconds $\Delta nA/mm^2/5$ s becomes smaller than specific change amount threshold values are shown in FIG. 16A and FIG. 16B. FIG. 16A illustrates when the response voltage E2 is applied, and FIG. 16B illustrates when the non-response voltage E1 is applied. Note that FIG. 16A is the same as FIG. 8. The change amount threshold value when the response voltage E2 is applied is set at 0.2 nA/mm$^2$ and the change amount threshold value when the non-response voltage E1 is applied is set at 0.5 nA/mm$^2$. As seen from these graphs, the period of time until the change in response current becomes small is earlier for thinner membrane thickness sensors CA3% Spin and CA2% Spin than for the thickest sensor CA4% Spin. The cause of this difference in time when the response voltage E2 is applied is postulated to be due to response delay based on the glucose permeability restriction by the CA membrane. The cause of this difference in time when the non-response voltage E1 is applied is postulated to be due to the difference in charge amount of the electric double layer on the electrode arising from the difference in states of the CA membrane. The time until the change of the response current becomes smaller is earlier in the sensors with simulated defective membranes CA4% Spin-A to -D than in the CA4% Spin sensor with completely covered surface.

Taking a normal state as a CA4% Spin sensor, by utilizing these results it is possible to ascertain a state in which the membrane thickness of the CA membrane has become thinned, and a state in which a portion of the CA membrane has been damaged, at the manufacturing stage or during use. In this case the change amount threshold value is 0.2 nA/mm$^2$ when the response voltage E2 is applied, and 0.5 nA/mm$^2$ when the non-response voltage E1 is applied, however the change amount threshold values are appropriately set according to such factors as the specification of the sensor section 4 and the sampling periods.

Figure 17:
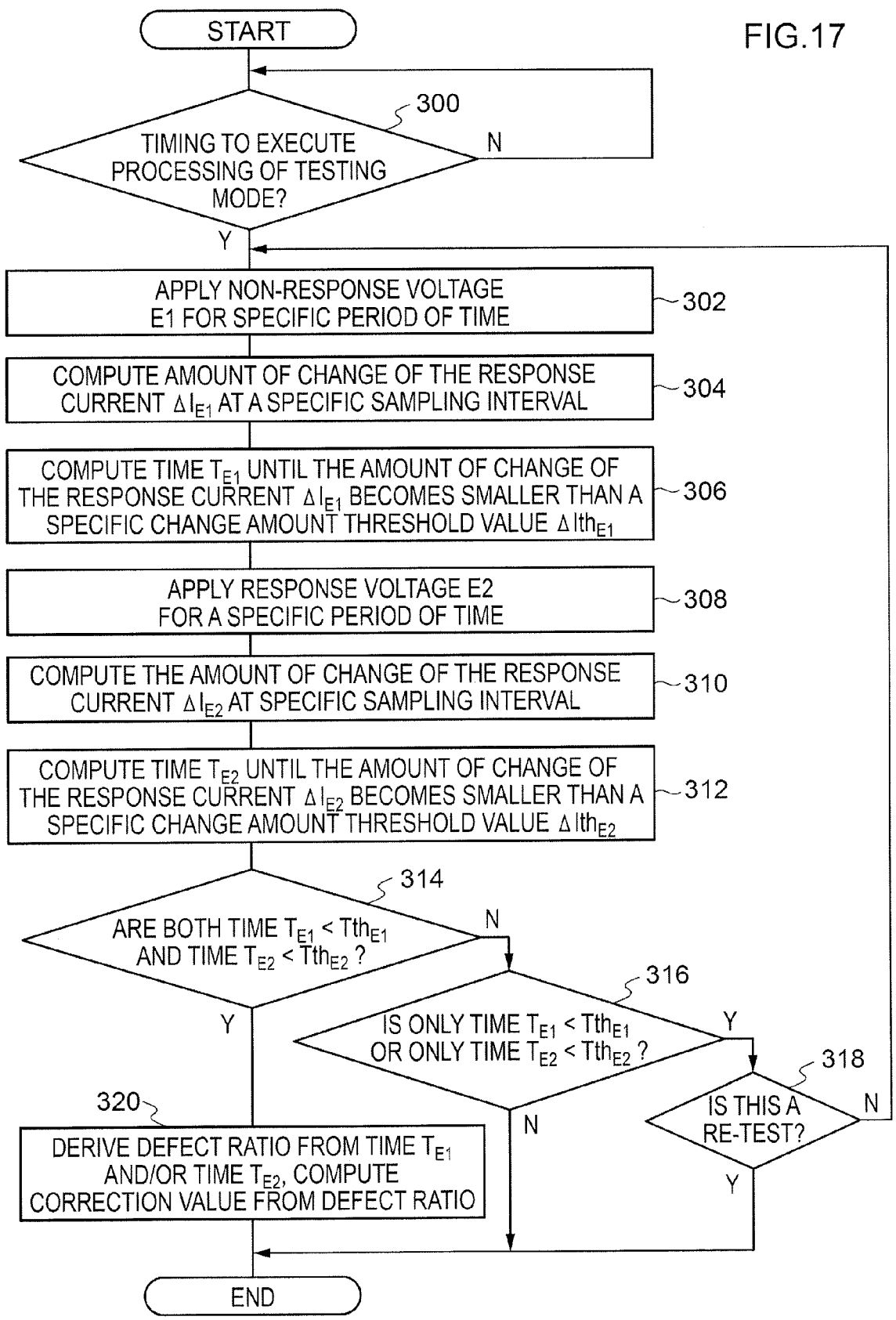
FIG. 17 is a flow chart illustrating a testing mode processing routine executed in a continuous glucose monitoring device of a third exemplary embodiment.

Explanation follows regarding a testing mode processing routine executed during the testing mode of the continuous glucose monitoring device 1 of the third exemplary embodiment, with reference to FIG. 17.

At step 300 determination is made as to whether or not it is a timing for executing the processing of the testing mode. Processing transitions to step 302 when determined that the execution timing for the testing mode has arrived. However when determined that the execution timing for the testing mode has not yet arrived determination at step 300 is repeated until determined that the execution timing has arrived.

In step 302 the non-response voltage E1 is applied for a specific period of time. For example a voltage of −200 mV is applied for 240 seconds. Then, in step 304, at a specific sampling interval (for example 5 seconds), the amount of change of the response current $\Delta I_{E1}$ is measured. Then at step 306, with the timing when the non-response voltage E1 is applied at step 302 as a starting point, the time $T_{E1}$ until the measured amount of change of the response current $\Delta I_{E1}$ becomes smaller than a specific change amount threshold value $\Delta Ith_{E1}$ is computed. Note that explanation is made of a case in which the amount of change of the response current $\Delta I_{E1}$ is an absolute value. However, it is not limited to an absolute value, and the actual value may be employed. In such a case, the time $T_{E1}$ until the amount of change of the response current $\Delta I_{E1}$ becomes larger than a specific change amount threshold value $\Delta Ith_{E1}$ is computed. In other words, the time $T_{E1}$ until the amount of change of the response current $\Delta I_{E1}$ reaches a value within a specific range can be computed. The same applies to the amount of change of the response current $\Delta I_{E2}$ mentioned below.

Then at step 308 the response voltage E2 is applied for a specific period of time. For example +400 mV is applied for 120 seconds. Then at step 310, at a specific sampling interval (for example every 5 seconds) the amount of change of the response current $\Delta I_{E2}$ is measured. Then at step 312, with the timing when the response voltage E2 is applied at step 308 as a starting point, the time $T_{E2}$ until the amount of change of the response current $\Delta I_{E2}$ becomes smaller than a specific change amount threshold value $\Delta Ith_{E2}$ is computed.

Then at step 314 comparison is made of the time $T_{E1}$ computed at step 306 and a time threshold value $Tth_{E1}$, and of the time $T_{E2}$ computed at step 312 and a time threshold value $Tth_{E2}$. Determination is then made as to whether or not both the time $T_{E1}$ is smaller than the time threshold value $Tth_{E1}$ and the time $T_{E2}$ is smaller than the time threshold value $Tth_{E2}$. The time threshold value $Tth_{E1}$ is set with reference to the time when the non-response voltage E1 is applied until the amount of change of the response current $\Delta I_{E1}$ becomes smaller than the change amount threshold value $\Delta Ith_{E1}$ for a case when a sensor with normal semi-permeable membrane 45 is employed. Similarly, the time threshold value $Tth_{E2}$ is set with reference to the time when the non-response voltage E2 is applied until the amount of change of the response current $\Delta I_{E2}$ becomes smaller than the change amount threshold value $\Delta Ith_{E2}$ for a case when a sensor with a normal semi-permeable membrane 45 is employed. For example, as shown in FIG. 16A, when the response voltage E2 applied with CA4% Spin as a normal sensor, the time threshold value $Tth_{E2}$ can be set at 70±α seconds. Similarly, as shown in FIG. 16B, when the non-response voltage E1 is applied with CA4% Spin as a normal sensor, the time threshold value $Tth_{E1}$ can be set at 58±α seconds. Here, α can be set between 5 to 20 seconds, for example. When both time $T_{E1}$<time threshold value $Tth_{E1}$ and time $T_{E2}$<time threshold value $Tth_{E2}$, determination is made that the state of the semi-permeable membrane 45 has changed, namely that a defect has occurred, and processing transitions to step 320. However, processing transitions to step 316 when either time $T_{E1}$≥time threshold value $Tth_{E1}$ and/or time $T_{E2}$≥time threshold value $Tth_{E2}$.

At step 316 determination is made as to whether or not the time $T_{E1}$ is smaller than the time threshold value $Tth_{E1}$ but the time $T_{E2}$ is equal to the time threshold value $Tth_{E2}$ or greater, or the time $T_{E1}$ is equal to the time threshold value $Tth_{E1}$ or greater but the time $T_{E2}$ is smaller than the time threshold value $Tth_{E2}$. Namely determination is made as to whether or not one or other of the times T is smaller than the respective time threshold values Tth. When negative determination is made, since both the times T are equal to the respective time threshold values Tth or greater, determination is made that the state of the semi-permeable membrane 45 has not changed, namely that it is normal, and processing is ended. However, when determined that only one of the times T is smaller than the time threshold value Tth processing transitions to step 318 where determination is made as to whether or not the processing of step 314 or step 316 is already a re-test. When the current processing is processing for the first time, processing returns to step 302 and the processing is repeated and a re-test performed. However, when the processing is already being performed as a re-test, the state of the sensor is determined to be normal and processing ended.

In step 320, a defect ratio of the semi-permeable membrane 45 is derived based on the time $T_{E2}$ computed at step 312, correction values for the response currents measured in the monitoring mode are computed according to the defect ratio, and stored in the storage section 35.

Figure 18A:
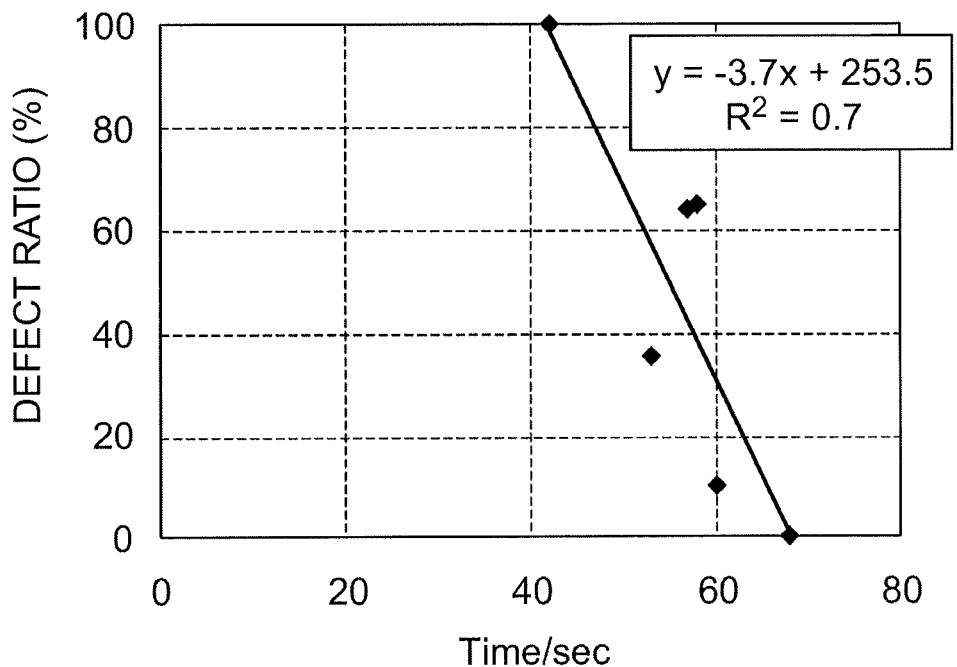
FIG. 18A and FIG. 18B are graphs illustrating a relationship between the time until the amount of change of the response current becomes less than a change amount threshold value with respect to a defect ratio, with FIG. 18A illustrating when a response voltage has been applied and FIG. 18B illustrating when a non-response voltage has been applied.
Figure 18B:
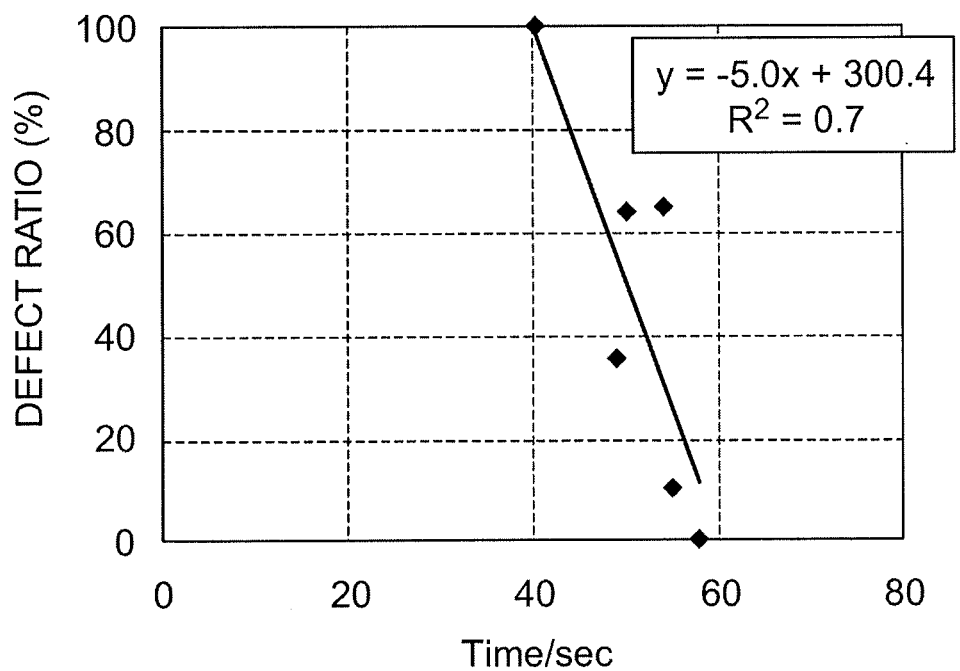

More specifically, first the relationship between the time $T_{E2}$ and the defect ratio is plotted, as shown in FIG. 18A. For instance, for each of the sensors shown in FIG. 6, the times $T_{E2}$ in the case the change amount threshold value $\Delta$Ith is set at 0.2 nA/mm² are computed, and the relationship between the times $T_{E2}$ and the defect ratios for each of the sensors are plotted on a graph with the horizontal axis as representing time $T_{E2}$ and the vertical axis as representing defect ratio. Note that FIG. 18A is the same as FIG. 10. A correspondence between the plotted time $T_{E2}$ and the defect ratio is derived and pre-stored in the storage section 35. The correspondence of the time $T_{E2}$ to the defect ratio is then employed to derive the defect ratio corresponding to a time $T_{E2}$ computed at step 312. For example, in the example of FIG. 18A, if the time $T_{E2}$ is 60 seconds then the defect ratio is derived as 31.5%. As shown in FIG. 18B, when determining the correspondence of the time $T_{E1}$ and the defect ratio, the defect ratio may be derived employing the time $T_{E1}$ computed at step 306. Alternatively configuration may be made such that both the defect ratio based on the time $T_{E1}$ and the defect ratio based on the time $T_{E2}$ are derived, and the average value, the larger value, or the smaller value of these defect ratios is then employed as the defect ratio. Then, as in the first exemplary embodiment, the derived relationship between the defect ratio and the sensitivity normal-error difference is employed to derive the sensitivity normal-error difference corresponding to the derived defect ratio.

As explained above, according to the continuous glucose monitoring device of the third exemplary embodiment, the times employed to test the state of the semi-permeable membrane 45 are both the time until the amount of change of the response current immediately after a voltage that obtains a response caused by glucose is applied becomes less than a predetermined threshold value, and the time until the amount of change of the response current immediately after a voltage that does not obtain a response caused by glucose is applied becomes less than a predetermined threshold value. Hence sensor state testing can be performed in a short time, stably and with good precision without providing plural sets of working electrodes and counter electrodes. In particular, since the change in response current immediately after voltage application is employed for testing, the execution time for the testing mode can be made shorter than in cases employing the time until the response current reaches a steady state. This is more efficient in cases such as the present exemplary embodiment in which continuous monitoring is performed.

In the third exemplary embodiment, explanation is given of a case in which a defect in a sensor is determined to occur when it has been determined that both the time $T_{E1}$ until the amount of change of the response current immediately after application of the non-response voltage E1 becomes smaller than a predetermined amount of change and the time $T_{E2}$ until the amount of change of the response current immediately after application of the response voltage E2 becomes smaller than a predetermined amount of change are less than specific respective threshold values ($Tth_{E1}$ and $Tth_{E2}$). However, configuration may be made such that a defect in a sensor is determined to occur when time $T_{E1} < Tth_{E1}$ alone. Since the response current to non-response voltage E1 is a background response current caused by the peculiarities of the sensor including the external layer membrane and excludes a response current caused by glucose, the determination precision can be raised by determining whether or not a defect is present in a sensor using the change in response current to the non-response voltage E1. Furthermore, in cases in which at least the amount of change to the response current to the non-response voltage E1 is employed together with additionally employing the amount of change in the response current to the response voltage E2, determination is then made employing changes in response current to two different voltages, and determination precision can be further raised.

Explanation has been given of a case in which the response voltage E2 is applied (steps 308 to 312) after applying the non-response voltage E1 in the third exemplary embodiment (steps 302 to 306). However configuration may be made such that first the processing of steps 308 to 312 are executed for applying the response voltage E2, and then the processing of steps 302 to 306 are executed for applying the non-response voltage E1.

In the third exemplary embodiment explanation has been given of cases in which the amount of change per specific period of time of the response current immediately after application of each of the voltages is used as the change of the response current, and the times until the amount of change becomes less than predetermined amounts of change are employed. There is, however, no limitation thereto and configuration may be made such that the rate of change or the pattern of change of response current immediately after application of each of the voltages is employed for the change of the response current.

Figure 19:
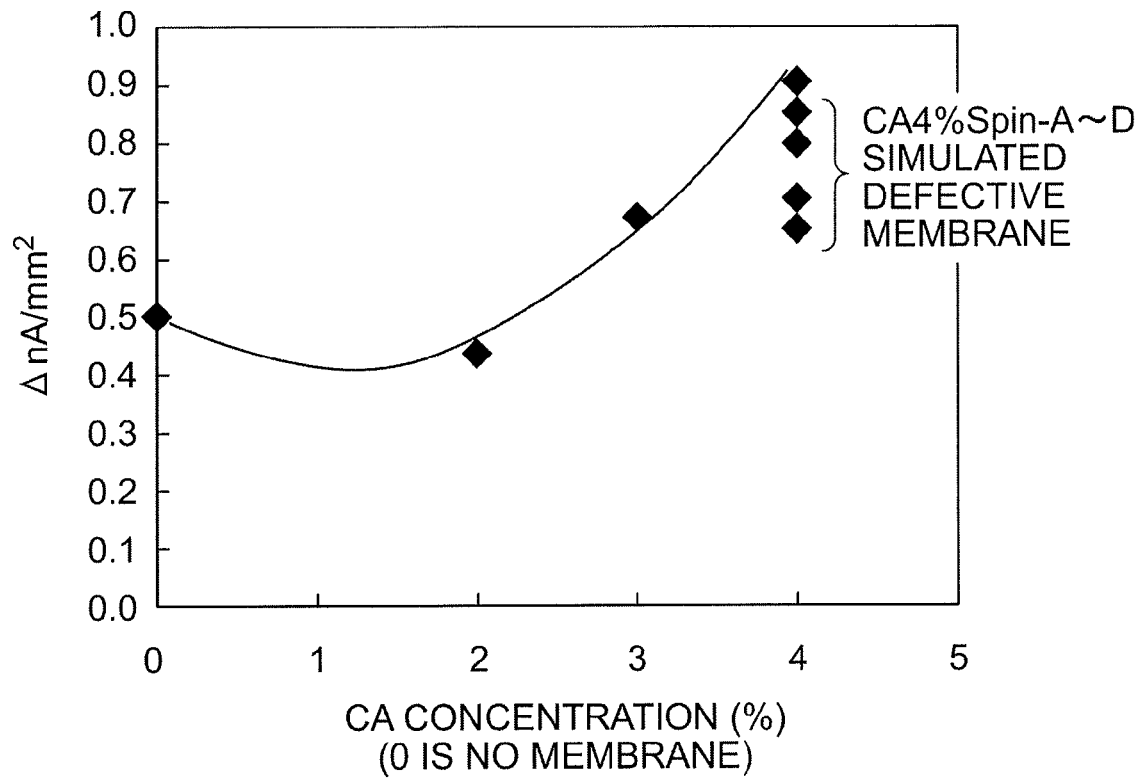
FIG. 19 is a graph illustrating the amount of change of the response current for each sensor with a different CA membrane state, when a non-response voltage has been applied.
Figure 20:
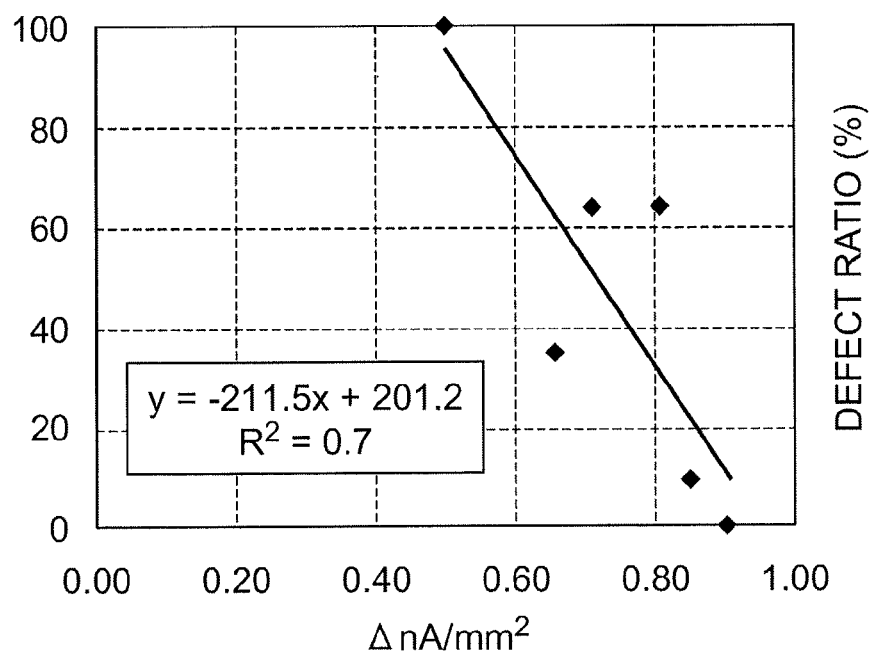
FIG. 20 is a graph illustrating a relationship between the amount of change of the response current with respect to a defect ratio when a non-response voltage has been applied.

Moreover, as in the second exemplary embodiment, the amount of change in the response current a predetermined period after application of the response voltage and the non-response voltage can also be employed. In such a case, the amount of change in the response current a predetermined period (here, 40 seconds) after application of the non-response voltage E1 (−200 mV) using each of the sensors shown in FIG. 6 is illustrated in FIG. 19. Note that the amount of change in the response current when the non-response voltage E1 is applied is the same as in FIG. 12. As seen from FIG. 19, the change in response current is smaller for thinner membrane thickness sensors CA3% Spin and CA2% Spin than for the thickest sensor CA4% Spin. The cause of this difference in time is postulated to be due to the difference in charge amount of the electric double layer on the electrode arising from the difference in states of the CA membrane. Moreover, the change of the response current is smaller in the sensors with simulated defective membranes CA4% Spin-A to -D than in the CA4% Spin sensor with completely covered surface. Using such a result, as in the second exemplary embodiment, a correspondence of the amount of change of the response current $\Delta I$ to the defect ratio can be determined as shown in FIG. 14 and FIG. 20.

Figure 21:
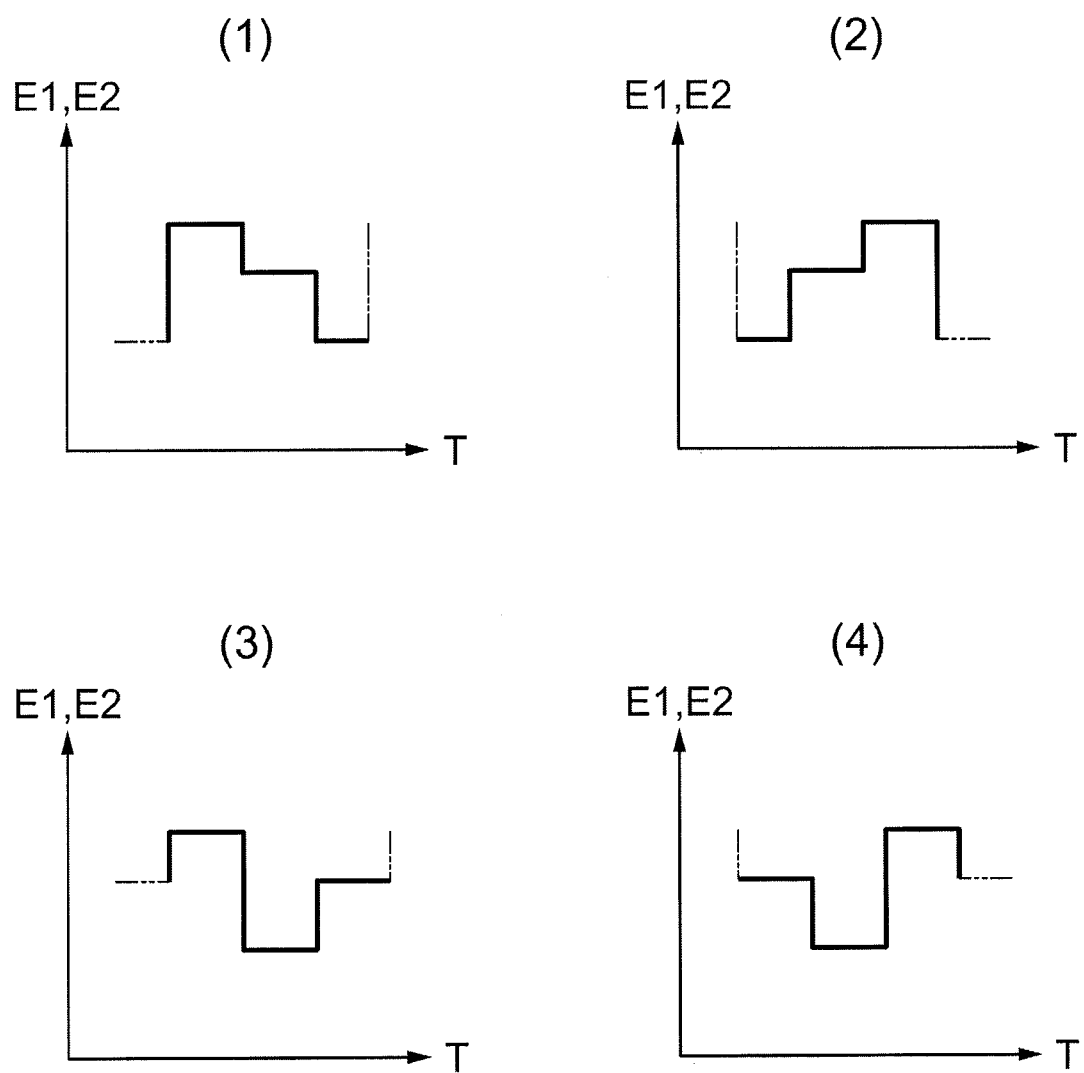
FIG. 21 shows diagrams illustrating other examples of voltage patterns.

Furthermore, in the third exemplary embodiment explanation has been given of cases of voltage patterns in which the non-response voltage E1 and the response voltage E2 are applied alternately, as shown in FIG. 5, however the voltage pattern does not need to always be a pattern in which the non-response voltage E1 and the response voltage E2 are applied alternately. For example, as shown in FIG. 21 (1) to (4), configuration may be made such that voltage application is in steps with combinations of plural constant voltages of different electrical potentials. Configuration may be made such that at a first step (a first step of a combination of a state in which the non-response voltage E1 is applied for a fixed period of time, and a state in which the response voltage E2 is applied for a fixed period of time) includes three constant voltages, as shown in FIG. 21 (1) to (4), however the number of constant voltages may be set at 2 or 4 or more. The testing frequency of the external layer membrane can accordingly be raised by the increase in the number of points at which electrical potential is changed.

Furthermore, in each of the above exemplary embodiments, explanation has been given of cases in which the analyzing device of the present invention is applied to a continuous glucose monitoring device, however monitoring target composition to be tested is not limited to glucose. Furthermore, application is not limited a CGM device and application can also be made to a Self-Monitoring of Blood Glucose (SMBG) device. In such cases configuration may be made such that testing is executed by the testing mode being selected by a user and a sample liquid being dripped on the sensor section by a user.

In each of the above exemplary embodiments explanation has been given of cases in which a correction value is computed when a defect in a sensor (semi-permeable membrane) is detected, however configuration may be made such that a signal indicating that a defect in a sensor has occurred is output when a defect in a sensor is detected, and a correction value is either computed for output with this signal or not even computed. In such cases configuration may be made such that an output unit and an alarm unit are provided to the analyzing device, and when a defect in a sensor is detected a signal indicating that a defect in a sensor has occurred is output from the output unit to the alarm unit. More specifically, a display, speaker or vibration unit may be provided as the alarm unit, such that a message that a defect in a sensor has occurred is displayed on the display, sound is output from the speaker, or the device is caused to vibrate when the alarm unit receives the signal from the output unit. Configuration may also be made such that the signal from an output unit is output for example to an external data processing apparatus and warning that a defect in a sensor has occurred is made by an alarm unit provided to the external data processing apparatus. Note that the configuration of the alarm unit is not limited to the examples referred to above.

In each of the above exemplary embodiments, explanation has been given of cases in which the response voltage or the non-response voltage is applied for specific periods of time. However configuration may be made such that that application of the response voltage or the non-response voltage is halted at the point in time when it is determined the amount of change of the response current is smaller than the change amount threshold value, and then the subsequent processing is executed.

Figure 22A:
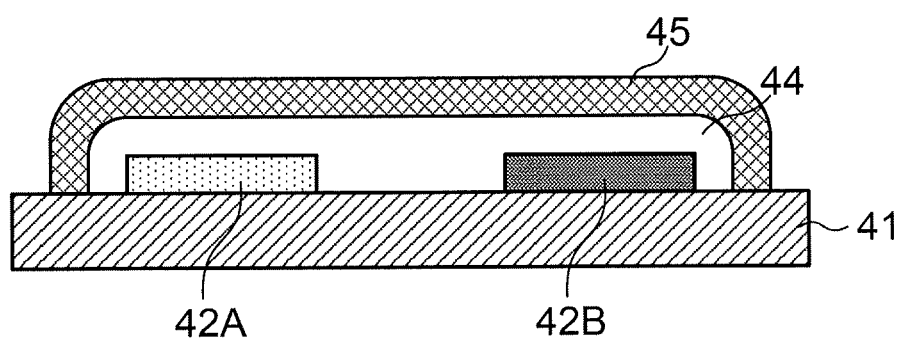
FIG. 22A and FIG. 22B show cross-sections illustrating other examples of end portions (electrode portions) of a sensor section.
Figure 22B:
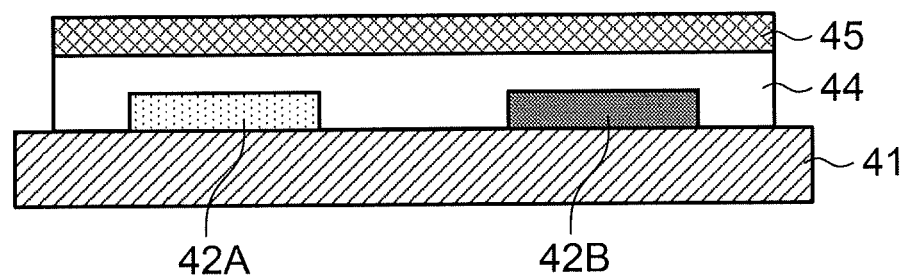

In each of the above exemplary embodiments, explanation has been given of cases in which the end portion of the sensor section (the electrode portion) is configured as the example shown in FIG. 3, however other configurations can be employed. For example, configuration may be made such that the semi-permeable membrane 45 is formed so as to cover a working electrode portion 42A and a counter electrode portion 42B as shown in FIG. 22(1), or a semi-permeable membrane 45 may be formed layered on a reagent layer 44 as shown in FIG. 22(2). Note that an enzyme portion 43 is disposed in a reagent layer above the working electrode portion 42A, although the enzyme portion 43 has been omitted from illustration in FIG. 22.

There are no particular limitations to the storage medium for storing a program of the present invention, and configuration may be made for example with a hard disk or with a ROM. Configuration may also be made with a CD-ROM, DVD disk, magneto-optical disk or IC card. Configuration may also be made such that the program is downloaded from a device such as a server connected to a network.

What is claimed is:

1. An analyzing device comprising:
   a sensor section comprising
      a reagent layer comprising a reagent capable of reacting with a target substance in a sample liquid,
      an electrode section comprising a first electrode and a second electrode for applying a voltage to the reagent layer, and an external layer membrane for contacting the reagent layer;
   a voltage application unit configured to apply at least one of a first voltage across the first electrode and the second electrode, resulting in a response current, caused by the target substance, flowing between the first electrode and the second electrode, and a second voltage resulting in no or substantially no response current;
   a current measurement unit configured to measure the response current flowing between the first electrode and the second electrode; and
   a computer programmed to compute at least one of
      a time required for an amount of change of the response current per specific amount of change in time resulting from the application of the first voltage to reach a value in a predetermined first specific range prior to when the response current reaches a steady state for determining whether there is a defect present in the external layer membrane or
      a time required for an amount of change of the response current per specific amount of change in time resulting from the application of the second voltage to reach a value in a predetermined second specific range prior to when the response current reaches a steady state for determining whether there is a defect present in the external layer membrane.

2. The analyzing device of claim 1 further comprising:
   a storage unit configured to store
      a first relationship between the time required for an amount of change of the response current per specific amount of change in time resulting from the application of the first voltage to reach a value in a predetermined first specific range and a set of defect ratios corresponding to the time required for the response current resulting from the application of the first voltage, and
      a second relationship between the time required for an amount of change of the response current per specific amount of change in time resulting from the application of the second voltage to reach a value in a predetermined second specific range and a set of defect ratios corresponding to the time required for the response current resulting from the application of the second voltage; and
   a correction unit configured to correct the response current value measured by the current measurement unit when a defect is determined by the determination unit to have occurred in the external layer membrane,
   wherein the correction is based on at least one of the first relationship stored by the storage unit or the second relationship stored by the storage unit.

3. The analyzing device of claim 2 wherein the correction unit is configured to estimate the defect ratios based on at least one of the first relationship and the second relationship, and to correct the response current value measured by the current measurement unit based on a relationship between the defect ratio of the external layer membrane and the response current value measured from the sensor section provided with an external layer membrane having defects corresponding to the defect ratio.

4. The analyzing device of claim 3 wherein the defect ratio based on both the first relationship and the second relationship is computed as the average value, the maximum value or the minimum value of a first defect ratio estimated based on the first relationship and a second defect ratio estimated based on the second relationship.

5. The analyzing device of claim 1 further comprising an output unit that is configured to output a signal indicating that a defect has occurred in the sensor section when a defect is determined to have occurred in the external layer membrane by the determination unit.

6. The analyzing device of claim 1 wherein the voltage application unit is configured to apply the first voltage and the second voltage alternately.

7. The analyzing device of claim 1 wherein the current measurement unit is configured to continuously measure the current flowing between the first electrode and the second electrode.

8. The analyzing device of claim 1 wherein the sensor section is configured to be disposed under the skin of a user of the analyzing device and the reagent layer is configured to react to a composition to be tested present under the skin.

9. The analyzing device of claim 1 wherein the reagent layer is configured to extract electrons from the composition to be tested and to supply the extracted electrons to the electrode.

10. The analyzing device of claim 1 wherein the reagent layer includes an enzyme portion for extracting electrons from the composition to be tested.

* * * * *